United States Patent
Cropper

(10) Patent No.: US 9,539,150 B2
(45) Date of Patent: Jan. 10, 2017

(54) APPARATUS FOR, AND METHOD OF, REDUCING KNEE PAIN AND/OR INCREASING LEVELS OF ATHLETIC PERFORMANCE

(76) Inventor: Dean Cropper, Talent, OR (US)

( * ) Notice: Subject to any disclaimer, the term of this patent is extended or adjusted under 35 U.S.C. 154(b) by 0 days.

(21) Appl. No.: 13/376,380

(22) PCT Filed: Jun. 7, 2010

(86) PCT No.: PCT/US2010/037666
§ 371 (c)(1),
(2), (4) Date: Dec. 5, 2011

(87) PCT Pub. No.: WO2010/141958
PCT Pub. Date: Dec. 9, 2010

(65) Prior Publication Data
US 2012/0078151 A1  Mar. 29, 2012

Related U.S. Application Data

(60) Provisional application No. 61/184,778, filed on Jun. 5, 2009.

(51) Int. Cl.
*A61F 13/00* (2006.01)
*A61F 13/06* (2006.01)
(Continued)

(52) U.S. Cl.
CPC ........... *A61F 13/062* (2013.01); *A61F 5/0106* (2013.01); *A61F 5/0109* (2013.01); *A61F 5/30* (2013.01); *A61F 5/34* (2013.01)

(58) Field of Classification Search
USPC ... 602/5, 16, 26, 23, 60; 128/882, 846, 869; 2/22, 237, 338, 227–228; 482/124; 606/204; 601/134
See application file for complete search history.

(56) References Cited

U.S. PATENT DOCUMENTS

| 1,607,032 A | * | 11/1926 | Whitley | ............. | A63B 71/1225 |
| | | | | | 2/22 |
| 4,162,672 A | | 7/1979 | Yazaki | | |

(Continued)

FOREIGN PATENT DOCUMENTS

CN  1383799 A  12/2002
CN  101219079  7/2008
(Continued)

OTHER PUBLICATIONS

USPTO, International Search Report for international patent application Ser. No. PCTUS1037666, dated Aug. 10, 2010.
(Continued)

*Primary Examiner* — Ophelia A Hawthorne
(74) *Attorney, Agent, or Firm* — Durham Jones & Pinegar, P.C.

(57) ABSTRACT

An apparatus for reducing knee pain or increasing athletic performance includes a compressive element, an elastic strap and, optionally, a hard actuator. The compressive element may be a sleeve a compressive wrap or a compressive pair of shorts configured to fit over a thigh of at least one leg. The elastic strap may be configured to fit tightly and circumferentially over and around the compressive element at a location above a knee joint at a mid-portion of the thigh. The hard actuator may be a generally concave-shaped element with a concave side. The elastic strap may be configured to fit over the hard actuator and to press the concave side of the concave hard actuator against a portion of an anterior side of the mid-portion of the thigh. With this configuration, the apparatus may reduce knee pain or increase athletic performance. Methods for reducing knee pain and increasing athletic performance are also disclosed.

18 Claims, 16 Drawing Sheets

(51) Int. Cl.
*A61F 5/30* (2006.01)
*A61F 5/01* (2006.01)
*A61F 5/34* (2006.01)

(56) References Cited

U.S. PATENT DOCUMENTS

| | | | |
|---|---|---|---|
| 4,182,338 A | 1/1980 | Stanulis | |
| 4,308,861 A | 1/1982 | Kelly | |
| 4,479,495 A | 10/1984 | Isaacson | |
| 4,590,939 A | 5/1986 | Sakowski | |
| 4,716,898 A | 1/1988 | Chauve | |
| 4,986,263 A | 1/1991 | Dickerson et al. | |
| 4,997,438 A | 3/1991 | Nipper | |
| 5,267,928 A * | 12/1993 | Barile | A63B 21/4025 |
| | | | 2/228 |
| 5,295,996 A | 3/1994 | Blair | |
| 5,556,374 A | 9/1996 | Grace | |
| 5,695,520 A | 12/1997 | Bruckner | |
| 5,735,807 A | 4/1998 | Cropper | |
| 5,893,871 A | 4/1999 | Tanaka | |
| 5,968,002 A * | 10/1999 | Morrisseau | A61F 5/0102 |
| | | | 128/869 |
| 6,007,503 A | 12/1999 | Berger | |
| 6,189,538 B1 | 2/2001 | Thorpe | |
| 6,711,750 B1 | 3/2004 | Yoo | |
| 6,773,411 B1 * | 8/2004 | Alvarez | A61F 5/0109 |
| | | | 602/27 |
| 7,389,547 B1 * | 6/2008 | Wiens | A41D 1/08 |
| | | | 2/227 |
| 7,757,307 B2 * | 7/2010 | Wong | A41B 9/02 |
| | | | 2/228 |
| 2003/0139698 A1 | 7/2003 | Hyson | |
| 2003/0187375 A1 * | 10/2003 | Gaylord | A61F 5/32 |
| | | | 602/26 |
| 2004/0162582 A1 | 8/2004 | Banziger | |
| 2004/0254505 A1 | 12/2004 | Begley | |
| 2005/0240134 A1 | 10/2005 | Brown | |
| 2010/0088803 A1 * | 4/2010 | Orloff | A41D 13/0015 |
| | | | 2/228 |

FOREIGN PATENT DOCUMENTS

| | | |
|---|---|---|
| DE | 94 17 221 U1 | 1/1995 |
| DE | 10 2005 017 587 A1 | 4/2006 |
| JP | H07-246212 A | 9/1995 |
| JP | 3091470 U | 11/2002 |
| JP | 2004-160075 A | 6/2004 |
| JP | 2008-178618 A | 8/2008 |

OTHER PUBLICATIONS

USPTO, International Preliminary Report on Patentability for international patent application Ser. No. PCTUS1037666, dated Jun. 11, 2011.

European Patent Office, "Supplementary European Search Report," mailed Jan. 22, 2015, in European patent application No. 10784239.5.

* cited by examiner

EMG Activity: Vastus Lateralis (VL)

EMG Activity: Vastus Medialis (VM)

EMG Activity: Lateral Hamstrings (LH)

EMG Activity: Medial Hamstrings (MH)

EMG Activity: Gluteus Maximus (GMAX)

APPARATUS FOR, AND METHOD OF, REDUCING KNEE PAIN AND/OR INCREASING LEVELS OF ATHLETIC PERFORMANCE

CROSS-REFERENCE TO RELATED APPLICATIONS

This application is a national stage entry of international application PCT/US2010/037666, filed on Jun. 7, 2010 and titled APPARATUS FOR, AND METHOD OF, REDUCING KNEE PAIN AND/OR INCREASING LEVELS OF ATHLETIC PERFORMANCE ("the '666 PCT Application"), filed under 35 U.S.C. §371 . The '666 PCT A claim for the benefit of priority to the Jun. 5, 2009 filing date of U.S. Provisional Patent Application No. 61/184,778 ("the '778 Provisional Application") was made in the '666 PCT Application pursuant to 35 U.S.C. §119(e). The entire disclosures of the '778 Provisional Application and the '666 PCT Application are hereby incorporated herein.

FIELD OF THE INVENTION

The present invention relates to an apparatus for, and method of, reducing knee pain and/or increasing at least one level of athletic performance. More particularly, the present invention relates to a leg apparatus and method that comfortably reduces knee pain and/or produces increased levels of athletic performance, particularly when jumping and/or running.

BACKGROUND OF THE INVENTION

Knee pain, as referenced herein, originates from several different structural or mechanical sources, for example, degenerative disease such as osteoarthritis, biomechanical dysfunction causing joint malalignment, and injury. Treatment methods vary based on the diagnosis, the severity of pain, and the training of the medical professional. Previous devices and methods to reduce knee pain include the following: (1) Prescription and over-the-counter pain medications; (2) Non-steroidal anti-inflammatory drugs ("NSAIDS") ("anti-inflammatories"); (3) Icing; (4) Injections, which fall into two categories—steroids and high molecular weight hyaluronan ("HMWH")-type injections; (5) Rigid knee bracing; (6) Soft bracing and taping; (7) Surgery; and (8) Physical Therapy.

Pain medications are not only expensive, but might cause side effects and may become addictive.

NSAIDS are very common in the treatment of knee pain. NSAIDS are taken orally and are generally anti-inflammatory in their effect. Disadvantages nevertheless include, among others, the long time required for them to produce any results, their wide variety in effectiveness, their great cost, and side effects caused by introducing synthetic chemicals into the body, such as, but not limited to, upset stomach, nausea, vomiting, heartburn, headache, diarrhea, constipation, drowsiness, unusual fatigue, stomach pain, swelling of the feet, and tinnitus.

Icing numbs pain and can reduce inflammation, but has limited benefits.

Injections are also designed to reduce pain. Steroids are designed to reduce inflammation and, thus, pain. Their effects last anywhere from a few weeks to a few months. HMWH injections are designed to create an artificial synovial fluid in a knee joint. This may take weeks to produce results, however, and the effectiveness varies dramatically. Injections are expensive, and also offer variable results.

Attempts to alleviate knee pain also include the application of load-bearing mechanical braces. These systems have several advantages in respect to achieving at least some degree of temporary relief. Rigid knee bracing, for example, is used to prolong the need for a total knee arthroplasty (TKA). Often called "unloaders," these braces provide a rigid frame around the knee actually to create a lever action from opposing sides of a knee, and typically take pressure off an affected (often medial) compartment of a knee joint. There is no healing as a result of wearing such brace, just reduced pain to one degree or another. Osteoarthritic "unloader" braces for instance are cumbersome, are prone to create discomfort themselves from their compressive contact points, and are expensive.

Soft bracing has also been used, sometimes using the same mechanical principals as rigid bracing. Soft bracing has historically been some type of wrap (early on non-elastic), but with the advent of the elastic wrap (ACE® wrap), it provided something more dynamic in its response to the knee joint, which imparted a degree of comfort and effectiveness. Elastic knits were next developed in the 1950s and '1960s. More highly developed elastic knits are still being used. In the early '1970s neoprene sheet stock anywhere from about 0.32 cm to about 0.64 cm in thickness was cut into patterns and sewn or glued together so that it could be pulled over the knee and fit approximately 12.7 cm-about 17.78 cm above the knee and about 5.1 cm-about 10.16 cm below it. In the '1990s another material, called BIO SKIN®, became available, which made wearing a soft brace more comfortable but still followed a similar design in which material was worn on opposing sides of a patella.

The general idea was to cover the knee area (but not the patella) and apply compression to the knee since the pain was being generated from the knee. Thus, soft bracing for pain relief has been designed to fit onto the knee or near the patellar tendon. Any compression to the distal end of the thigh, knee, and proximal calf, was to cover the knee joint. Some braces even represent efforts to reduce the amount of material on the thigh or calf, and thereby focus on compressively surrounding only the knee joint itself. These types of soft bracing carry certain disadvantages, however. The ill-fitting nature of most designs behind the knee in the popliteal area has always been a challenge to the wearer because of discomfort.

Surgery and physical therapy likewise have, in most cases, the prolonged drawbacks of discomfort and pain.

Unfortunately, current practices in almost all cases for knee pain fall into one of these above-identified categories.

For producing increased levels of human performance there are no known methods other than performance enhancing drugs. The concept of actually increasing human performance without such drugs is unknown. The ability to increase performance instantly has been a long sought after goal for many years. E.I. du Pont de Nemours and Company, in conjunction with William Kraemer, Ph.D., conducted a five year study at Pennsylvania State University wherein they found that compression garments sustained, but did not actually increase, the immediate performance abilities of trained and untrained athletes. The Kraemer study looked at the effects of fatigue, power, and endurance with high compression and high elastic garments. Although the study found that athletes were perhaps able to maintain their ability to perform at their previously known level, data showed nothing more than a sustained level of performance. From this study and other Kraemer works, we see that swimmers now wear different apparel, and tennis players wear compression sleeves on their arms.

Hence, the prior art fails to provide an apparatus or method that adequately reduces knee pain and/or increases lower extremity performance levels.

BRIEF SUMMARY OF THE INVENTION

Thus, the present invention is directed to an apparatus that provides an easy and/or effective way to reduce or eliminate knee pain.

The present invention is alternately or additionally directed to a method that provides an easy and/or effective way to reduce or eliminate knee pain.

The present invention is alternately or additionally directed to an apparatus that provides an easy and/or effective way to increase levels of athletic performance.

The present invention is alternately or additionally directed to a method that provides an easy and/or effective way to increase levels of athletic performance.

One aspect of the present invention is directed to an apparatus for reducing knee pain and/or increasing athletic performance, comprising a compressive sleeve, a compressive wrap, or a compressive pair of shorts configured to fit over a thigh of at least one leg; and an elastic strap configured to fit tightly and circumferentially over and around the compressive sleeve, the compressive wrap, or the compressive pair of shorts, above a knee joint at a mid-portion of the thigh; wherein no portion of the apparatus covers or contacts an exterior portion of the knee joint; and wherein application of the apparatus reduces knee pain and/or increases athletic performance.

In another aspect, the apparatus further comprises a generally concave-shaped hard actuator having a concave side, wherein the elastic strap is configured to fit over the hard actuator and thereby press the concave side of the hard actuator against a position on an anterior side of the mid-portion of the thigh.

In yet another aspect, the position is approximately over the intersection of the rectus femoris muscle, the Sartorius muscle, and the vastus medialis obliquus muscle.

In still another aspect, the generally concave-shaped hard actuator is generally oval-shaped, and has a shallow concave-shape, thereby making it generally flat.

Another aspect of the invention is directed to an apparatus for reducing knee pain and/or increasing athletic performance, comprising a compressive sleeve, a compressive wrap, or a compressive pair of shorts configured to fit over a thigh of at least one leg; and an elastic strap configured to fit tightly and circumferentially over and around the compressive sleeve, the compressive wrap, or the compressive pair of shorts, above a knee joint at a mid-portion of the thigh; the apparatus not being operatively positioned at opposing sides of a knee joint and thus not providing direct anatomical alignment of either a patella, or a femoral or tibial condyle, with respect to another portion of the knee joint; and wherein application of the apparatus reduces knee pain and/or increases athletic performance.

Another aspect of the invention is directed to an apparatus for reducing knee pain and/or increasing athletic performance, comprising a compressive sleeve, a compressive wrap, or a compressive pair of shorts configured to fit over a thigh of at least one leg; an elastic strap configured to fit tightly and circumferentially, over and around the compressive sleeve, the compressive wrap, or the compressive pair of shorts, above a knee joint at a mid-portion of the thigh; a generally concave-shaped hard actuator having a concave side, wherein the elastic strap is configured to fit over the hard actuator and thereby press the concave side of the hard actuator against a position on an anterior side of the mid-portion of the thigh; wherein application of the apparatus reduces knee pain and/or increases athletic performance.

Another aspect of the invention is directed to an apparatus for reducing knee pain and/or increasing athletic performance, comprising a compressive sleeve, a compressive wrap, or a compressive pair of shorts configured to fit over a thigh of at least one leg; and an elastic strap configured to fit tightly and circumferentially over and around the compressive sleeve, the compressive wrap, or the compressive pair of shorts, above a knee joint at a mid-portion of the thigh; wherein the apparatus decreases the firing intensity of a vastus medialis obliquus muscle relative to its firing intensity without the apparatus; and wherein application of the apparatus reduces knee pain and/or increases athletic performance.

In still another aspect, the mid-portion of the thigh is a distal third mid-portion of the thigh.

Another aspect of the invention is directed to an apparatus for reducing knee pain and/or increasing athletic performance, comprising a thigh component configured to fit over a thigh of at least one leg; an elastic strap configured to fit tightly and circumferentially over and around the thigh component, above a knee joint at a mid-portion of the thigh; a generally concave-shaped hard actuator having a concave side, wherein the elastic strap is configured to fit over the hard actuator and thereby press the concave side of the concave hard actuator against a position on an anterior side of the mid-portion of the thigh; wherein application of the apparatus reduces knee pain and/or increases athletic performance.

Another aspect of the invention is directed to an apparatus for reducing knee pain and/or increasing athletic performance, comprising a thigh component configured to fit over a thigh of at least one leg; an elastic strap configured to fit circumferentially over and around the thigh component, above a knee joint at a mid-portion of the thigh; an actuator having a side that operatively faces the thigh and operatively comprises and/or defines at least one enclosed space, the elastic strap being configured to fit over the actuator and thereby press the side of the actuator against a position on an anterior side of the mid-portion of the thigh; wherein application of the apparatus reduces knee pain and/or increases athletic performance.

In another aspect, the space is at least partially hollow, gel-filled, or liquid-filled.

In yet another aspect, the side is concave-shaped.

In still another aspect, application of the apparatus allows a wearer to achieve more than a sustained level of maximum athletic performance, which exceeds a previous, or what would otherwise be an absolute, level of athletic performance by the wearer.

In yet another aspect, the apparatus allows the wearer to achieve at least about a 2.4 average percent increase in performance level.

In still another aspect, the apparatus reduces pain by an amount that is at least a therapeutically effective amount of pain reduction.

Another aspect of the present invention is directed to a method of reducing knee pain, comprising applying at least one of a tight compression sleeve, a tight elastic strap, and a hard actuator, that is compressed over and against a portion of a medial-side of a wearer's thigh, at a lengthwise mid-point of a wearer's thigh away from the wearer's knee joint on the same leg; wherein the application of the at least one of a tight compression sleeve, tight elastic strap, and hard actuator decreases the activity or firing intensity of the thigh's vastus medialis obliquus muscle and increases the activity or firing intensity of the leg's gluteus maximus.

Another aspect of the invention is directed to a method of reducing knee pain and/or increasing athletic performance that uses any one or more of the above-recited aspects.

Yet another aspect of the invention is directed to any apparatus or method comprising any one or more of the above-recited features and/or any one of the specific features recited hereinbelow, used singly or in combination, whether including past or future known feature(s) or not.

BRIEF DESCRIPTION OF THE DRAWINGS

In the accompanying drawings, which form a part of the specification and are to be read in conjunction therewith, and in which like reference numerals are used to indicate like parts in the various views:

FIG. 2 is an exploded plan view showing attachment positioning of an elastic strap onto a compression sleeve component of the apparatus of FIG. 1a;

FIG. 3 is a plan view showing attachment of a strap onto a compression sleeve component of the embodiment of FIG. 1a;

FIG. 6a is a top perspective plan view of the concave actuator of the embodiment of FIG. 1a;

FIG. 6b is a side-bottom perspective view of the concave actuator of the embodiment of FIG. 1a;

FIG. 6c is a diagonal top-distal-side perspective view of the concave actuator of the embodiment of FIG. 1a;

FIG. 6d is a top-proximal perspective view of the concave actuator of the embodiment of FIG. 1a;

FIG. 6e is a top-side perspective view of the concave actuator of the embodiment of FIG. 1a;

FIG. 6f is a bottom-side perspective view of the concave actuator of the embodiment of FIG. 1a.

FIGS. 8a-d are graphs showing electromyographic data of vastus lateralis muscles used with, and without, application of the embodiment of FIG. 1a;

FIGS. 9a-d are graphs showing electromyographic data of vastus medialis muscles used with, and without, application of the embodiment of FIG. 1a;

FIGS. 10a-d are graphs showing electromyographic data of lateral hamstrings muscles used with, and without, application of the embodiment of FIG. 1a;

FIGS. 11a-d are graphs showing electromyographic data of medial hamstrings muscles used with, and without, application of the embodiment of FIG. 1a;

FIGS. 12a-d are graphs showing electromyographic data of gluteus maximus muscles used with, and without, application of the embodiment of FIG. 1a; and FIGS. 13a-b are graphs showing average muscle force normalized to body weight when used with, and without, application of the embodiment of FIG. 1a.

DETAILED DESCRIPTION OF THE INVENTION

As illustrated in the accompanying drawings and discussed in detail below, one aspect of the present invention is directed to an apparatus that provides an easy and/or effective way to reduce or eliminate knee pain, and/or immediately increase absolute levels of athletic performance.

In one embodiment, the apparatus of this aspect of the present invention does not cover any portion of the knee, and yet provides striking relief to those who suffer from knee pain. This discovery is so contrary to any type of thinking or treatment of the knee. For example, the knee pain treatment world has always looked at the knee itself when bracing to reduce pain while using the knee. This embodiment nevertheless works by an entirely different principle. By engaging soft tissue above the knee joint, which helps provide motion, structure, and sensation to the knee, it is believed that this embodiment initiates a complicated series of events to relieve pain and/or enhance athletic performance of the knee and its connective structures.

Figure 1A:
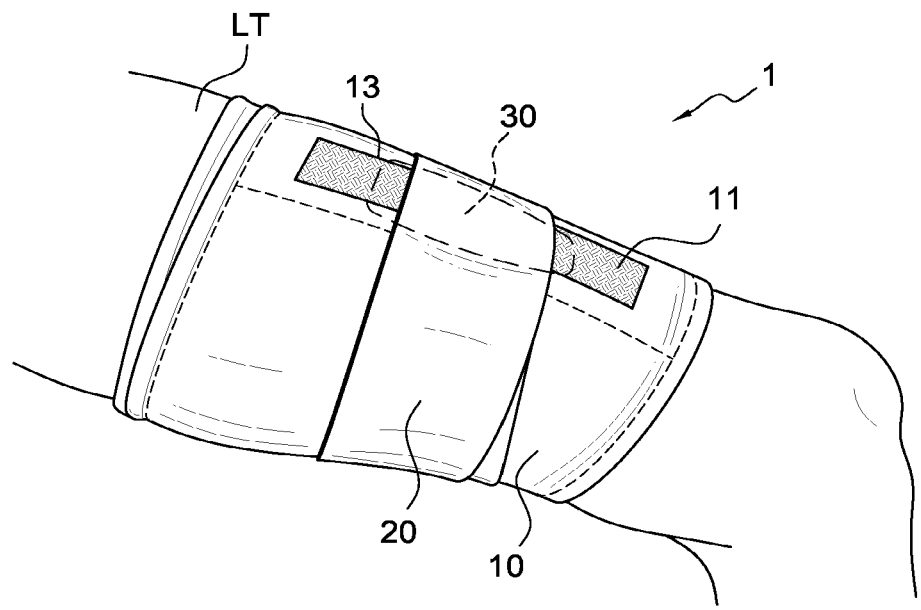
FIG. 1a is a medial side perspective view of one embodiment of an apparatus worn on a left leg, according to the present invention.

Referring to FIG. 1a, apparatus 1 provides a level of high compression to left thigh LT that changes the muscular firing sequence in normal knees within the wearer's quadriceps, hamstrings, and gluteal muscles. It is believed that this change in firing sequence changes the load and bio-dynamics within the knee joint. The combination of a sleeve 10, a strap 20, and an (optional) actuator 30, when placed over the junction of the rectus femoris ("RF") and vastus medialis obliquus ("VMO") muscles, in particular, appear to change the firing sequence in the quadriceps, change the swing phase in the gait of a wearer, and make it easier for the wearer to walk because the muscular structure is uniquely tensioned by strap 20 and actuator 30. At the same time, this embodiment is also surprisingly easy to apply and extremely comfortable to wear.

Several of the benefits of this embodiment include that it immediately works to diminish and/or eliminate knee pain. First and foremost, this embodiment has provided immediate pain relief for thirty-three of thirty-seven patients thus far responding to confidential requests for preliminary testing. As shown below, initial testing illustrates that it has worked immediately, for example, on several long-term chronic patients who have been using orally administered pain medications for years. By wearing apparatus 1, patients have thereby prolonged knee use without resorting to surgery, have rehabilitated their knee to improve function, and/or have dramatically reduced their narcotic and non-narcotic pain medication intake significantly or entirely.

Second, the ease of application makes this apparatus so much more preferable than soft or rigid bracing.

The ease in wearing the apparatus is likewise a third significant benefit.

The cost of treating knee pain to the patient is also reduced dramatically, which is a forth significant benefit.

By contrast, traditional thinking would apply, among other things, bracing over the pain area, i.e., over the knee. Thus, the use of an apparatus that works away from a painful knee site is surprising technology, especially considering that, when worn, this embodiment requires no physical contact with the knee joint. The general concept of using a thigh sleeve for problems unrelated to knee pain is not new by itself, because soft compression thigh sleeves are at times placed over the thigh for quadriceps and hamstring injuries with the understanding that compression over an injury site decreases pain. Conversely, traditional knee braces are sufficiently long to come up on the distal portion of a thigh but these are designed and used exclusively so that the rest of the brace actually fits over the knee or to provide an opposing point of leveraging contact to affect direct mechanical realignment of a knee. The concept of applying a device away from the knee to relieve knee pain is ground breaking, however.

And yet it has been determined that apparatus 1 is effective in reducing or eliminating knee pain. The high level of compression by sleeve 10 and the banding compression at thigh LT mid-section of both hamstring and quadriceps by strap 20 provides a significant level of instant relief. With actuator 30 enclosed in a pocket 13 of sleeve 10, the level of pain relief is maximized.

Thus, the application of a sleeve 10 for knee pain is unique. In consulting with experts, the inventor of the present invention has found that there has never been a product that has been used for delivering treatment for pain relief to the knee via a thigh device. Sleeve 10, used in conjunction with an actuator 30, which may be convex-and-concave-shaped hard plastic, placed into sleeve 10, is also original and inventive. Utilizing strap 20 (over actuator 30 or without actuator 30 and) around the thigh is also original and inventive.

Apparatus 1 is for use to reduce pain in individuals with, for example, osteo-arthritis in either femoral/tibial or patellofemoral ("PF") joint, general PF pain (which affects approximately one of four people to a greater or lesser degree), and general knee pain. It is specifically useful at least for relieving pain due to general patellofemoral dysfunction, PF osteoarthritis, femoral-tibial osteoarthritis, general knee pain, post total knee replacement surgery, post-operative knee surgery followed by ongoing pain, and/or post-traumatic knee pain.

Apparatus 1 may also be used to instantly increase human performance in at least jumping length. To date there has been significant improvement in jumping lengths in three athletes (2 male and 1 female). All athletes who have worn the device felt they were faster. For performance enhancement, this apparatus can be used by any athlete, professional or amateur, for increasing their athletic performance.

In one embodiment, apparatus 1 includes three components: (1) sleeve 10, (2) strap 20, and (3) actuator 30.

Thigh Component

A wearer, medical professional or other person applies sleeve 10 by inserting the wearer's leg into sleeve 10 and/or pulling, pushing, rolling, or otherwise moving it up and onto the wearer's thigh(s).

A suitable material for sleeve 10 is an elastic material, such as LYCRA®/film/ or LYCRA® laminate. These materials have low profiles and no skin reaction properties. Other elastic materials, such as neoprene or elastic knit, could work, but would add bulk, weight, and discomfort. In particular, apparatus 1 is made by cutting and sewing material such as BIO SKIN® into a tubular shape or flat so as to be able to wrap around the thigh at least once and attach onto itself, fastened, for example, by sewing or releasably attachable hook and loop fabrics.

One embodiment of this material is described in U.S. Pat. No. 5,735,807, which is hereby incorporated herein in its entirety. In particular, such material is made of three layers that are laminated and/or bonded together to produce a thin material having what is referred to as four-way stretch capability. The material has two outer layers of fabric, such as nylon, each having four-way stretch capability. The middle or center layer (membrane) is of polyurethane material that also has a four-way stretch capability. The outer layers and the center layer are laminated (bonded) together to provide a material that has characteristics beneficial for the present invention. The material, produced by laminating the layers together is thin, is very pliable, has great strength, has four-way stretch capability, has high elasticity retention and has a porosity factor on the order of about 35%.

This particular material is readily formed (fabricated) into a desired configuration by conventional sewing techniques since it is thin and very pliable. The material thickness is on the order of about 0.063 cm to about 0.114 cm, although it may be produced in other thicknesses to suit a particular application.

Thread or cord utilized to join (sew) the edges of the material at its seam(s) is preferably of an elastic material and the stitching is of a known type that provides the seam with substantially the same stretch capability as the material. It will be appreciated that the edges may be joined together by other known methods, such as by adhesively bonding the two edges together or by laser or ultrasonic welding. The pliability in conjunction with the four-way stretch capability of the material (and the seam(s)) permits the material readily to conform to a thigh.

In one embodiment, woven elastics having fewer or no seams are used.

The four-way stretch capability and the elasticity of the support applies a uniform retentive force and a mild compressive force to the area of the thigh that the support surrounds. Thus, apparatus 1 resistively conforms to the changes inherent to the flexing of the thigh muscles. That is, as the thigh is flexed, the muscles associated with the thigh area flex and change in their diametral size and the material allows apparatus 1 to elastically conform to the changes but, at the same time, apply a consistent resistive force to the area that the apparatus surrounds. Slow expansion is accomplished with little resistive force, whereas rapid expansion is accomplished with strong resistive force. Thus, a resulting sleeve, wrap, or pair of shorts is comfortable for slow movements and produces binding support to resist rapid expansion due to stressful movements of the thigh.

An additional benefit of this particular, thin material is its porosity factor, which is on the order of about 35%. The porosity of this material allows air to flow through the material and yet allow the material to have a heat retention property. This material thereby allows some air flow (breathing) through the material. The heat retention quality allows some external air (heat or cold) from entering, and some internal air (body heat) from exiting, through the material. The unique properties of this material help retain therapeutic heat while still allowing breathability (air flow) to reduce perspiration buildup.

In one embodiment, a particular construction of this material is from (a) an elastic material, such as LYCRA® fabric available from Darlington Fabrics, Style No. 7043 and (b) polyurethane membrane, one mil (about 0.00254 cm) thick produced by Fabrite Laminators, Style No. 6100. Materials (a) and (b) are laminated using a process including heat, pressure, and glue. The process as optimized produces a laminate that requires at least 25 psi to detach or delaminate the material.

Apparatus 1 is worn on either leg, or with two such apparatuses—one on each leg at the same time.

In one embodiment, apparatus 1 is applied by pulling sleeve 10 over a leg so that actuator 30, which is enclosed in pocket 13, is over the mid-portion of the thigh and so that the outside perimeter boundary of actuator 30 is in the center of the thigh.

Figure 1B:
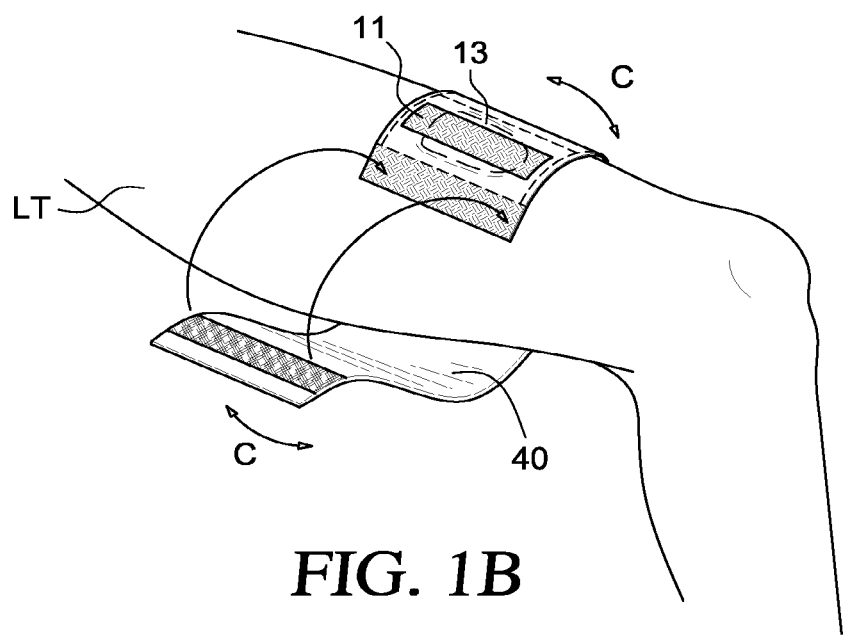
FIG. 1b is a medial side perspective view of an alternate embodiment of an apparatus worn on a left leg, according to the present invention.

Referring to FIG. 1b, in an alternate embodiment, apparatus 1 may be worn as wrap 40, which can be circumferentially adjusted to a correct position before application along direction arrows C. This design as a wrap-around is for easier application, particularly for overweight wearers.

In one embodiment, apparatus 1 is applied by wrapping wrap 40 over a leg so that actuator 30, which is enclosed in pocket 13, is positioned over the mid-portion of the thigh and so that the outside perimeter boundary of actuator 30 is in the center of the thigh. In one embodiment, wrap 40 is wrapped from the lateral to the medial side of the thigh.

Figure 1C:
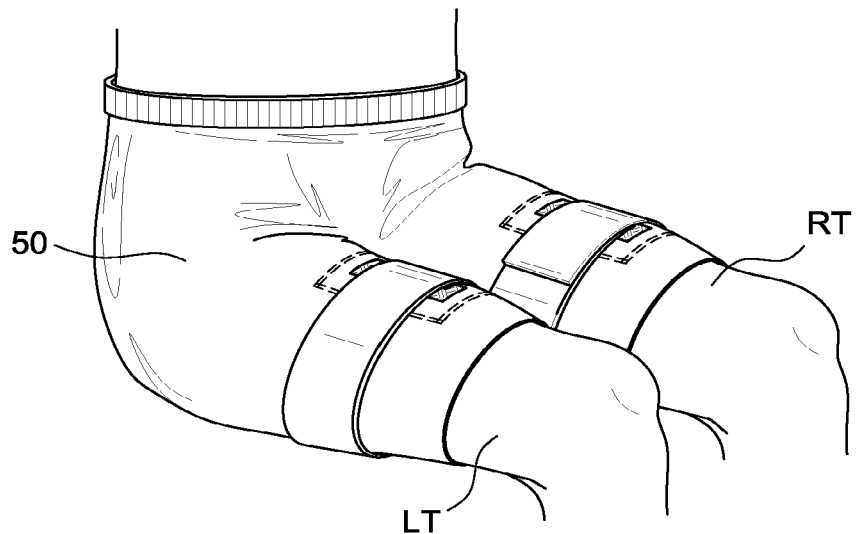
FIG. 1c is a medial side perspective view of yet another embodiment of an apparatus worn on a lower torso and legs, according to the present invention.

Referring to FIG. 1c, in another alternate embodiment, a pair of shorts 50 may be pulled up to the waist and worn on the thighs. Shorts 50 provide the option of a unilateral or a bi-lateral approach to the application of apparatus 1. When designed into a pair of shorts, apparatus 1 is functional for both pain and performance. This design makes it a bit more technically difficult to position actuator 30 over the optimal spot on the thighs since there is no easy ability to rotate the sleeves around the leg since the sleeves are attached to the short. As such specially-designed, or custom fit shorts can be tailored. Shorts 50 would fit around the waist with a length of the thigh 51 of shorts 50 running almost as far down the thigh as the knee, and in one embodiment at least about 5.08 cm above, or below, the knee.

Figure 1D:
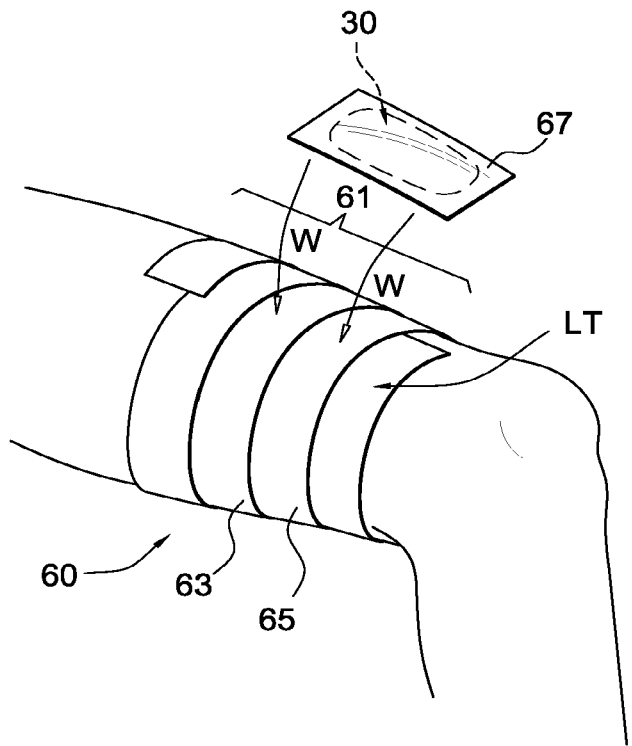
FIG. 1d is a medial side perspective view of still another embodiment of an apparatus wrapped multiple times around a thigh, according to the present invention.

Referring to FIG. 1d, in one embodiment, a band wrap 60 is wrapped multiple times around thigh LT. Such a band wrap 60 may be wrapped any number of times, from just once up to hundreds or even thousands of times, as a bandage or cord with at least one successive or distant circumferential length wholly or partially overlapping, or running beside, another such length. As an example, one band 63 partially overlaps a portion of the width of another band 65. In one embodiment, band wrap 60 attaches to itself by hook and loop fabric on its opposing sides. Bands 61 need not touch one another, however, and may be spaced apart to form a spiral type of wrapping. Bands 61 may overlap one another, wrap side-by-side, be spaced apart from each other, or be configured in any combination thereof. Bands 61 may be formed of fabric pieces or even very thin cord, for example, and be tapered and/or have changing and/or variable widths, thicknesses and material compositions.

Because bands 61 are covered in a hook or loop fabric, pocket 67, which has respective hook or loop-friendly fabric, is attached to band wrap 60 in accordance with directional arrows W, to position actuator 30. However, any fastening device or placement configuration suitable to position and secure the one or more additional pieces of this embodiment, several of which are as described below, can be used.

In one embodiment, any one or more of the above-described and referenced fastening device(s) and/or placement configuration(s), including a compression sleeve, shorts, or a band wrap, may be used singly or in combination with another, either on the same leg or in variance between a right and left leg.

Figure 1E:
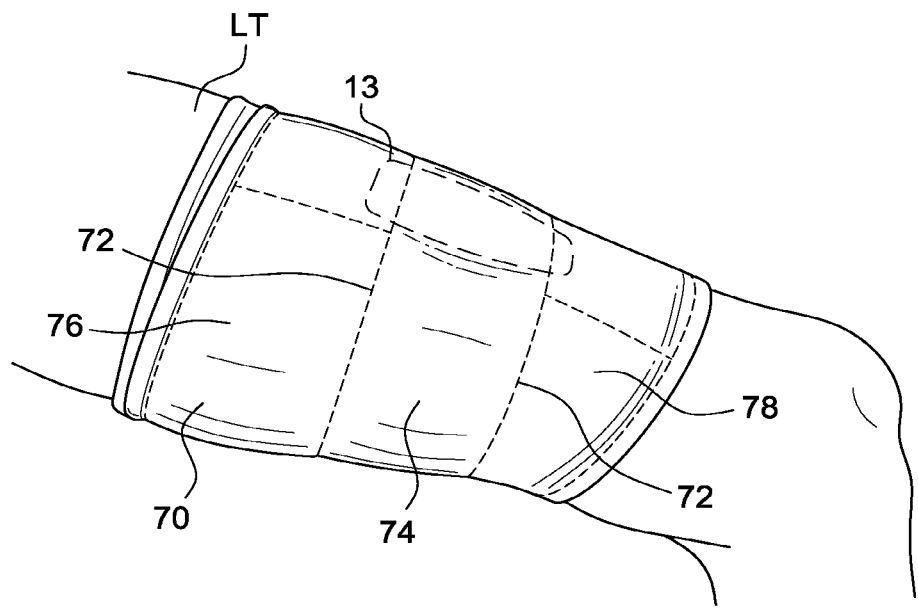
FIGS. 1e-f are medial side perspective views of yet another embodiment of an apparatus, worn on a leg and by itself, according to the present invention.
Figure 1F:
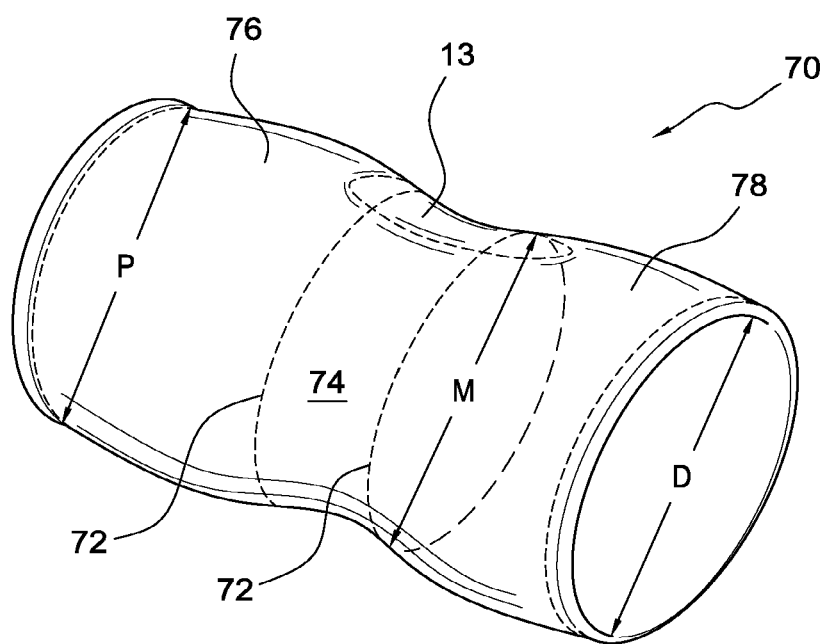

In one embodiment, any one of, e.g., a compression sleeve, compression shorts, or band wrap may be used without a strap or an actuator. Referring, for example, to FIGS. 1e and 1d, sleeve 70 is generally constructed like sleeve 10, but has, for example, a sewing-reinforced 72 internal portion 74, which is dimensioned and configured to be substantially more narrow in its internal circumferential diameter and, thus, tighter than either proximal portion 76 or distal portion 78 of sleeve 70. Internal portion 74 is a length of fabric material dimensioned e.g., by using a shorter length of material, to fit over the same portion of a thigh as, for example, strap 20 (above) and/or actuator 30 (below), and in particular can be dimensioned and positioned to fit over the same muscular position(s).

Thus, lines P and D, which represent the internal—at rest, non-stretched and non-expanded—diameters of proximal portion 76 and distal portion 78, are longer than line M, which represents the internal—at rest, non-stretched and non-expanded—diameter of mid-point, internal portion 74. M can be anywhere from about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% shorter than D and/or P, depending on the material and wearer's body type. Any similar configuration, which provides a sufficiently tighter fitting material around the mid-portion of the thigh, e.g., specifically around the thigh such that it fits centrally, or in part, over the junction of any or all of the rectus femoris muscle, the Sartorius muscle, or the vastus medialis obliquus muscle is suitable, however. Shorts of one embodiment similarly have a narrower internal circumferential dimension for placement at a mid-portion of a thigh, and a band wrap of this embodiment is more tightly wound at a mid-portion of a thigh, specifically at a position as indicated above. In one embodiment, actuator 30 fits into pocket 13, which allows actuator 30 to be inserted, removed, and replaced by a user with a different actuator 30 or the same actuator 30.

Strap

Figure 2:
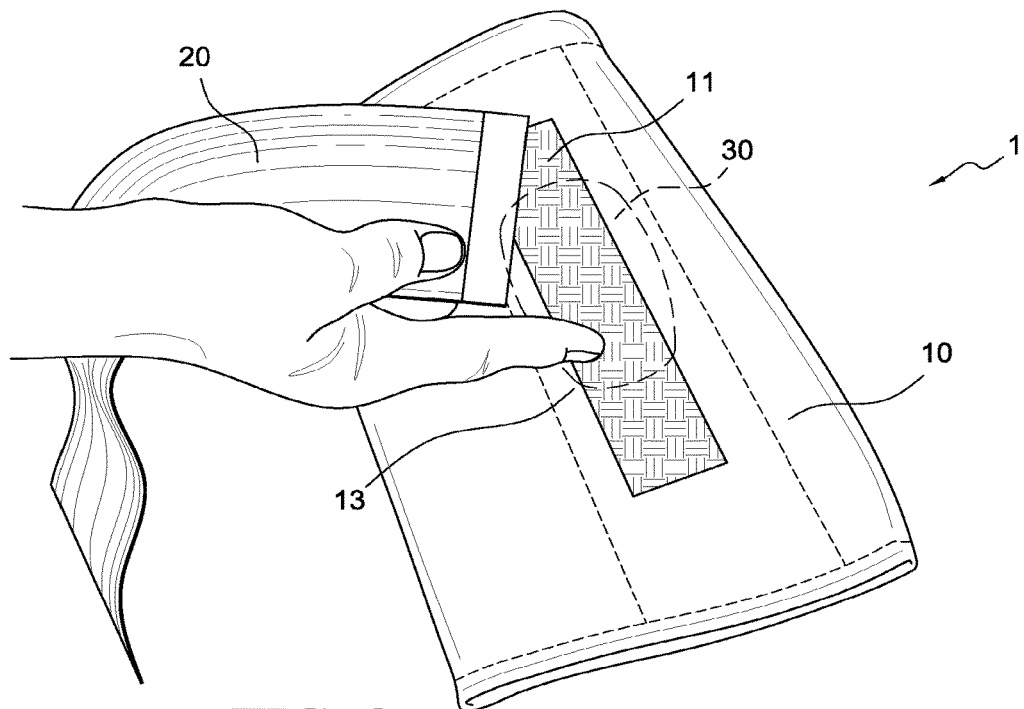
Figure 3:
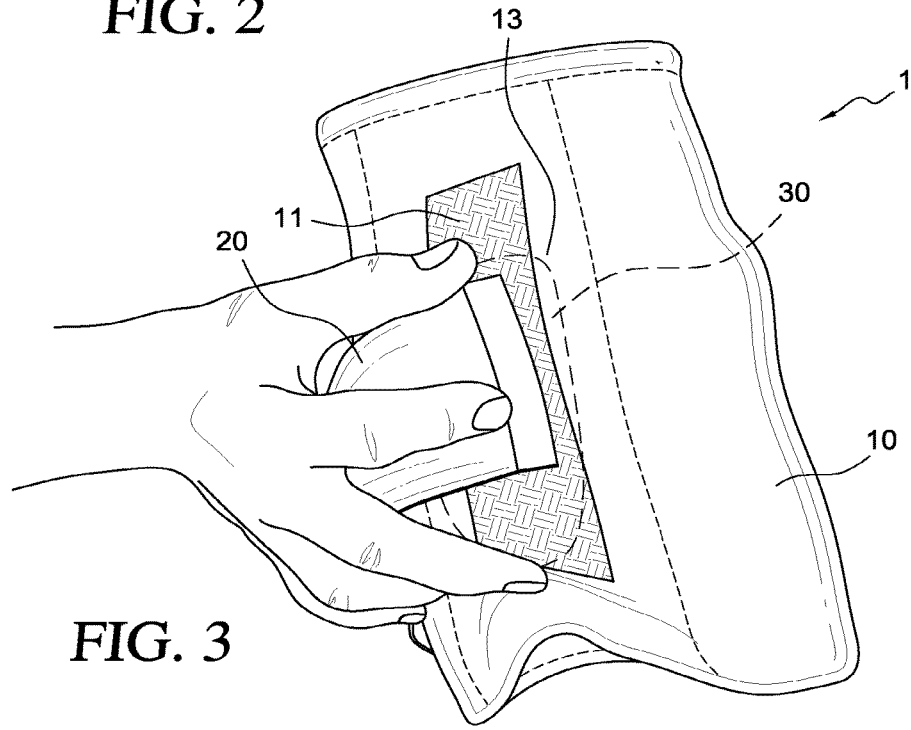

Referring to FIGS. 2 and 3, strap 20 is attached to a piece of loop fabric 11 sewn onto sleeve 10 adjacent to pocket 13, in which actuator 30 is sewn. The position of loop fabric 11 is more for convenience to make strap 20 easier to wrap in to provide effectiveness for apparatus 1. Thus, any positioning of loop fabric 11 (or hook fabric), or any fastening mechanism suitable for attaching and firmly compressing sleeve 10 is useful in this embodiment. Strap 20 is attached to a piece of loop fastener that is sewn onto the thigh component adjacent to the pocket 13 actuator 30 is in. Strap 20 is medially wrapped circumferentially around the thigh and attached at its opposing ends with the hook and loop fasteners.

Strap 20 may be separate and attached with hook and loop material, but it may also be sewn on permanently. Strap 20 around may have the elastic wrap permanently attached to the end of the wrap but a separate component is preferable.

In one embodiment, strap 20 is positioned circumferential to a mid-portion of a thigh, specifically at a distal third mid-portion of a thigh. However, other suitable mid-thigh positions may be used in this aspect of the invention.

In one embodiment, strap 20 is wrapped from the lateral to the medial side of the thigh. Thus, in one embodiment, strap 20 is wrapped in a medial direction around the thigh, although in an alternate embodiment, it is wrapped laterally.

Actuator

Figure 4:
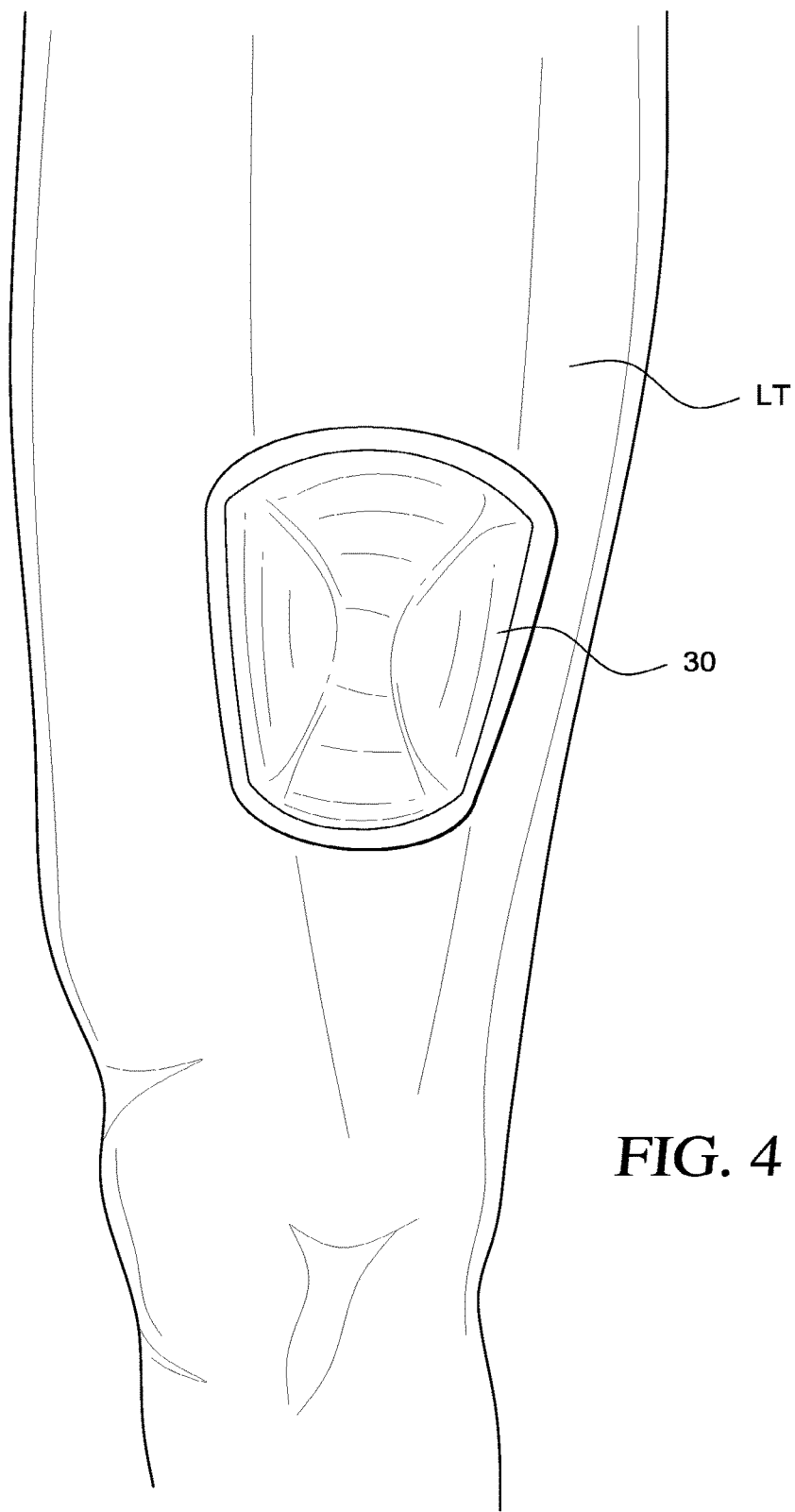
FIG. 4 is a plan view showing relative operative positioning of a concave actuator of the embodiment of FIG. 1a, with respect to the anterior side of a human thigh.
Figure 5:
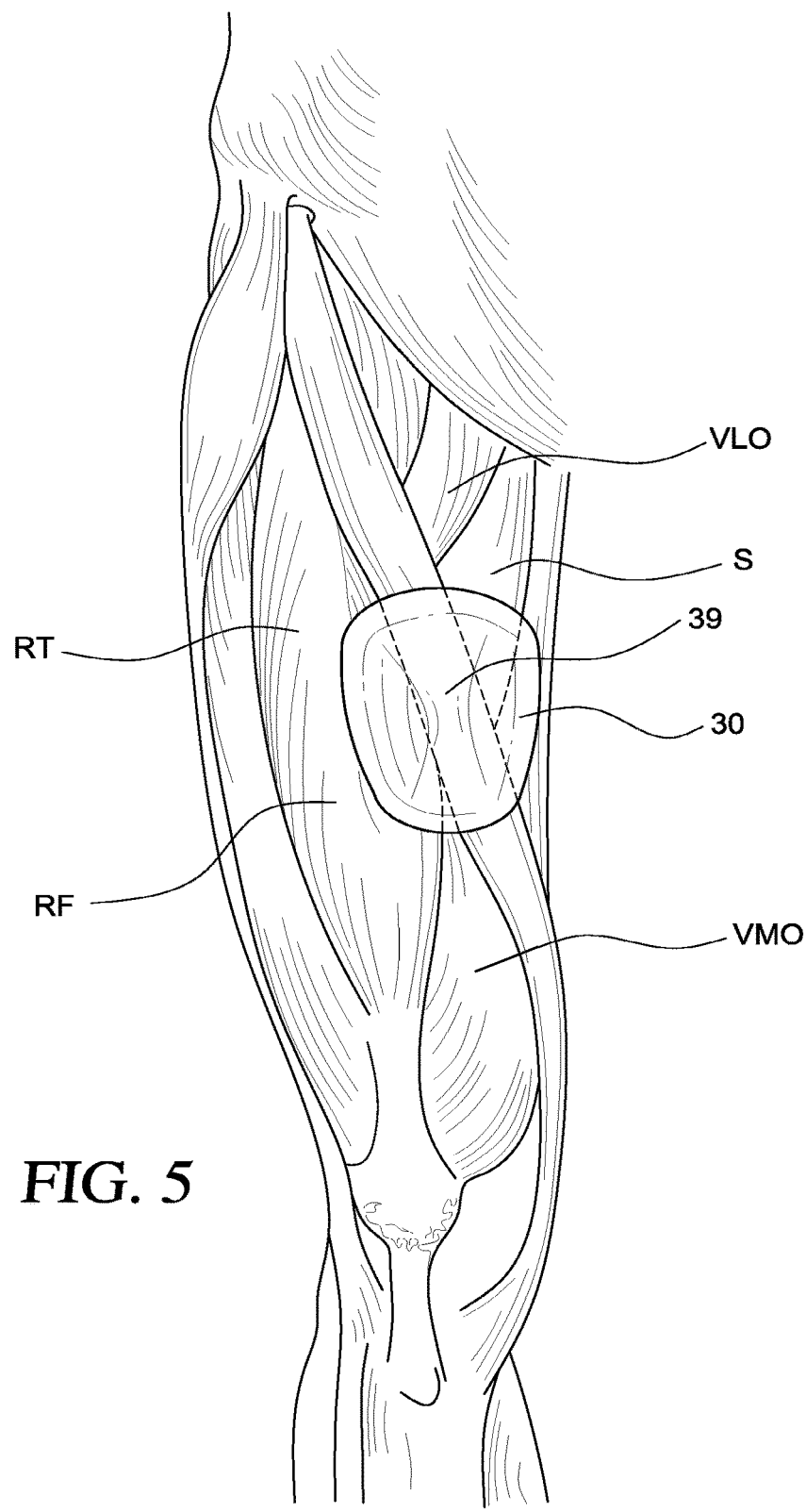
FIG. 5 is a partial plan view showing relative operative positioning of a concave actuator of the embodiment of FIG. 1a, with respect to the internal muscular and nervous system anatomy of the anterior side of a right human leg.
Figure 6A:
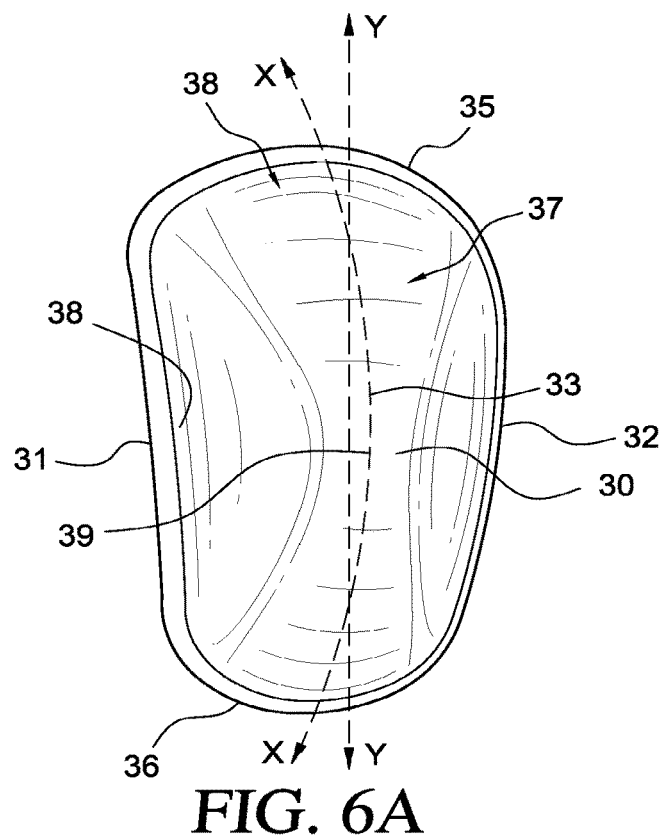
Figure 6B:
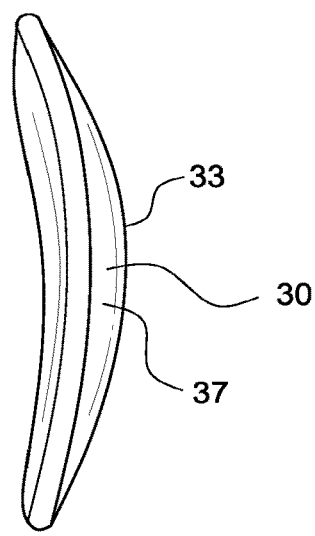
Figure 6C:
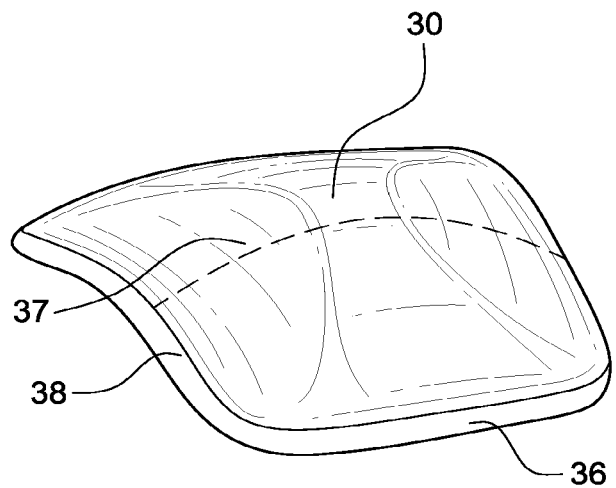
Figure 6D:
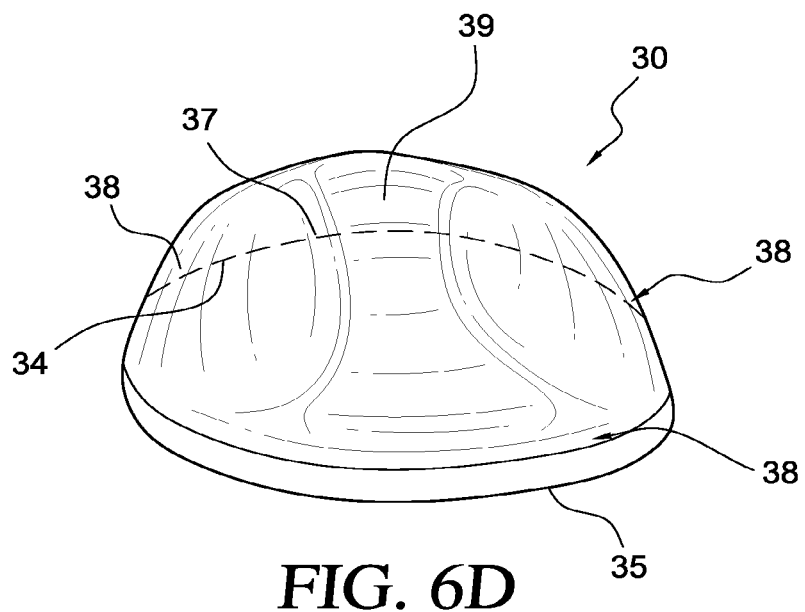
Figure 6E:
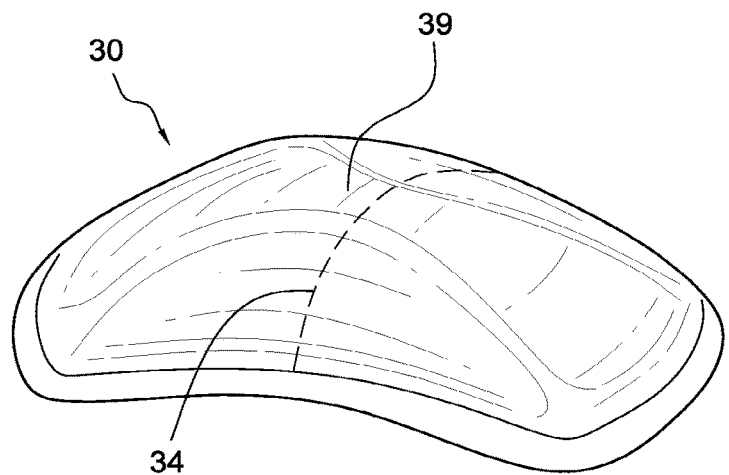
Figure 6F:
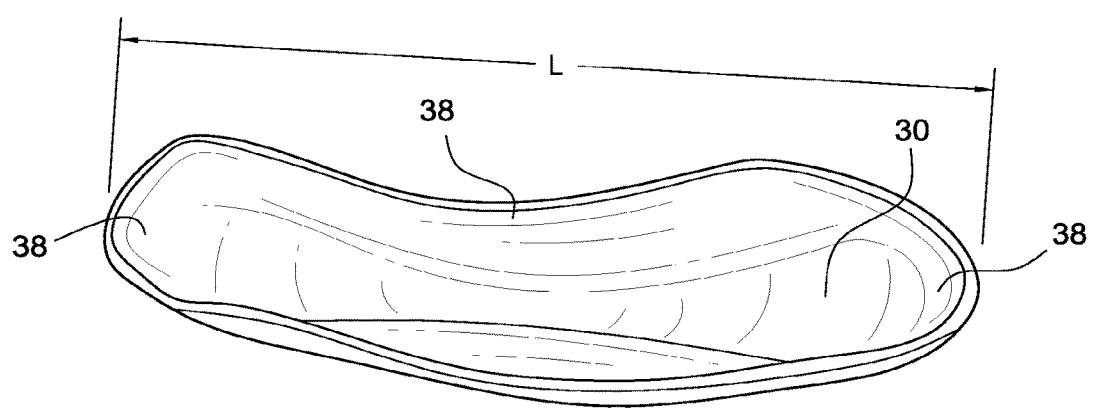

Referring to FIGS. 4 and 5, this positioning of actuator 30 specifically places the horizontal and vertical midpoint 39 of actuator 30 squarely over the medial side of the mid-portion of a thigh. In particular, the longitudinal and vertical midpoint 39 of actuator 30 is positioned over the junction of the VMO, rectus femoris ("RF"), and Sartorius ("S") muscles. This position places midpoint 39 over a branch of the femoral nerve ("FN").

In one embodiment, actuator 30 is positioned at a mid-portion of a thigh, specifically at a distal third mid-portion of a thigh. However, other suitable mid-thigh positions may be used in this aspect of the invention.

Thus, actuator 30 (and apparatus 1) does not in any way touch or impinge upon the knee. Its only connection to the knee is being placed over the muscles, nerves, and other soft tissue above the knee joint.

Referring to FIGS. 6*a-f*, actuator 30 is an injected molded hard plastic nylon component that is approximately 0.20 cm thick. Actuator 30 is about 10.2 cm long from end-to-end directly across its (unflattened) surface, which is its longest dimension and runs along its lengthwise axis of symmetry Y. This length dimension L is straight across and, thus, does not account for the length added by an upper curved lengthwise surface arc 33 (running above straight axis Y) that, if extended, would define a circle having about a 15.2 cm radius at the above-mentioned central lengthwise axis. (Upper curved lengthwise surface arc 33 is coaxial to and, if extended, the same as circular line X.) Actuator 30 has widths of approximately 8.26 cm and about 6.35 cm at the respective widest and narrowest width dimensions, which are defined by and run directly between two relatively straight tapering opposing sides 31 and 32. These width dimensions do not account for an upper curved widthwise surface arc 34 that, if extended, would define a circle having about a 7.62 cm radius at a width about halfway between the opposing ends of the tapering side lengths 31 and 32. The entire actuator 30 is bordered by a relatively more curved lip arc 38 around its upper surface to make a perimeter boundary of actuator 30. This lip arc 38, if extended, would define a circle having about a 2.54 cm radius. Its relatively straight opposing sides are connected at their relatively farther (separated by about 8.26 cm) and closer (about 6.99 cm) ends by respective rounded opposing side arcs, each of which, if extended, would define a circle respectively having about a 5.1 cm or about a 4.45 cm radius.

Actuator 30 is also generally rounded around its entire perimeter to form a generally flat, yet convexly shaped piece, with a length of about 15.24 cm and a width of about 7.62 cm along the slightly curved material top surface. These general dimensions can be modified depending on the size of a wearer's leg, however.

Thus, actuator 30 is applied to the body counter-intuitively. Concave surface 37 is actually applied against left thigh LT. Actuator 30 fits into pocket 13 in sleeve 10 and, when it is applied to a thigh (either as a pull-on sleeve, a wrap 15, or shorts 17) or introduced into pocket 13, actuator 30 is positioned medial to the rectus femoris and over the proximal body of the vastus medialis obliquus. In short, actuator 30, which fits snugly into pocket 13, which is sewn snugly to fit the dimensions of actuator 30, is directed more medially mid-thigh.

In one embodiment, concave surface 37, or the lower side of actuator 30, which operatively faces a thigh, comprises and/or defines at least one internal or perimeter, hollow or liquid-filled or gel-filled, space (such as but limited to, a gap, a trough, a hole, a cubby, a divot, or a channel). Non-limiting example shapes of such space(s) are semispherical, concave, domelike, cube, rectangular, box, open, or another regular or irregular and amorphous shape(s). These may for example also include, but are not limited to, pyramidal, cone, wavy, bumpy, cylindrical, nub-shaped, and/or irregular or odd shape(s).

For example, these one or more hollow, liquid-filled or gel-filled spaces can be defined by one or more main or auxiliary lips, or by one or more concentric or adjacent, internal or perimeter, lips—any of which are at the boundary of, or internal to, the lower face. This/these space(s) may be enclosed or open (the later thus forming part of the main perimeter boundary edge of the actuator).

In another embodiment, the hollow and/or liquid-filled space comprises ridges, grooves, or perimeter and/or internal brush, bristle, or other, relatively-soft and/or flexible projections—that project at any or multiple angle(s) with respect to a direction operatively normal to the thigh.

In one embodiment, actuator 30 comprises and/or defines multiple independent pieces or segments, having varying or same hardnesses, either from piece-to-piece, or along or within a single piece or segment.

In one embodiment, actuator 30 comprises and/or defines an enclosed or open space merely or additionally comprising a square, polygonal, circular, continuous or broken, irregular and/or elongated, ring or band.

In one embodiment, any array and/or combination of such or additional types of spaces may be used.

Figure 7A:
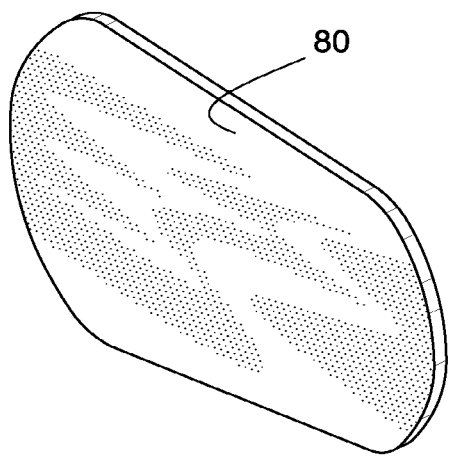
FIGS. 7a-c are respectively, perspective, top, and side views of an alternate embodiment of an actuator, according to the present invention.
Figure 7B:
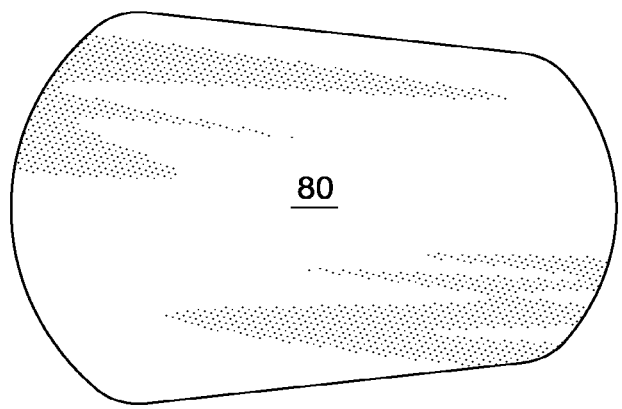
Figure 7C:
Figure 8A:
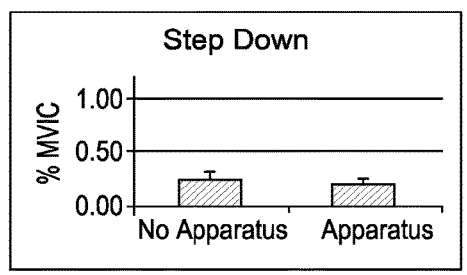
Figure 8B:
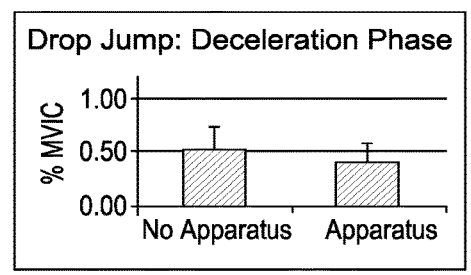
Figure 8D:
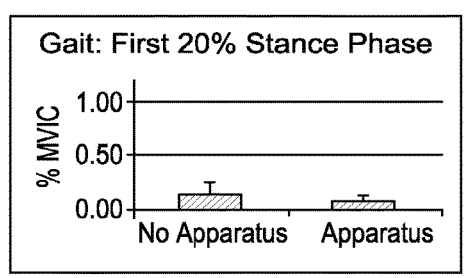
Figure 8C:
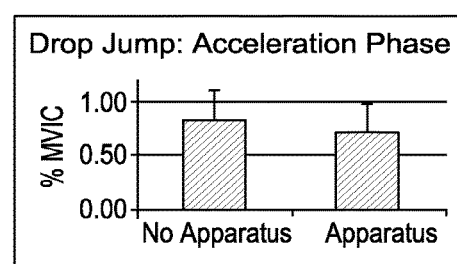
Figure 9A:
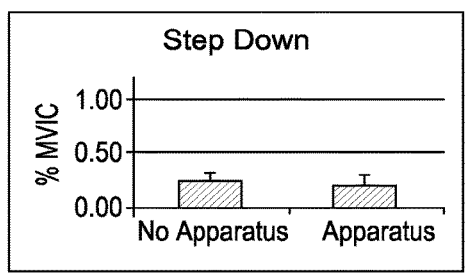
Figure 9B:
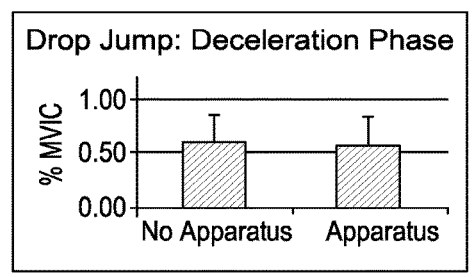
Figure 9D:
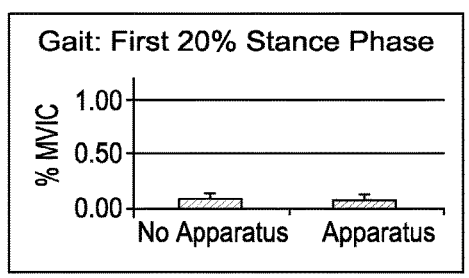
Figure 9C:
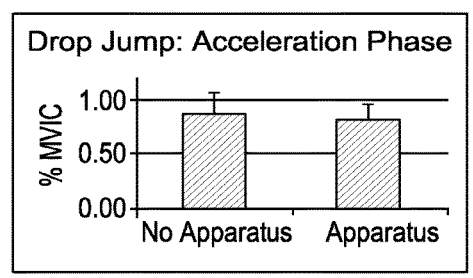
Figure 10A:
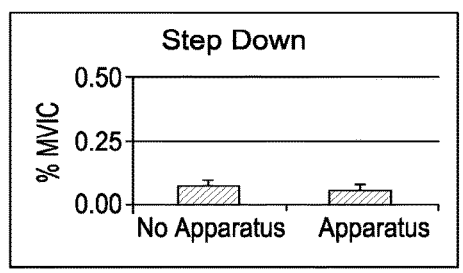
Figure 10B:
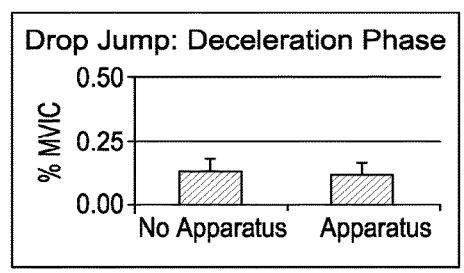
Figure 10D:
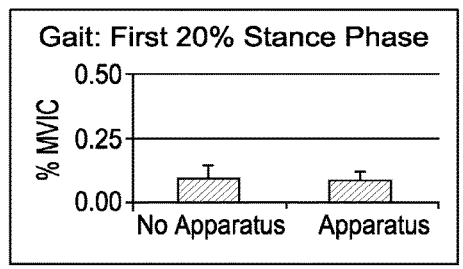
Figure 10C:
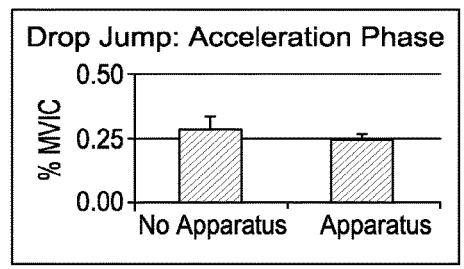
Figure 11A:
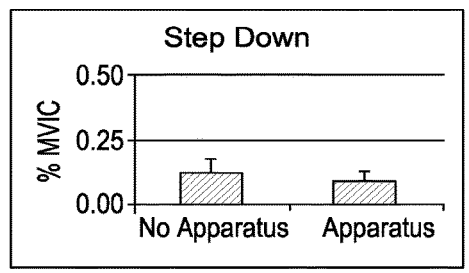
Figure 11B:
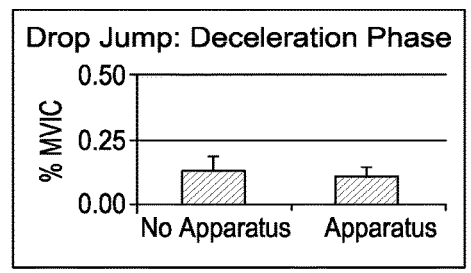
Figure 11D:
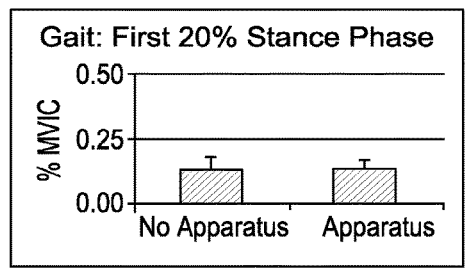
Figure 11C:
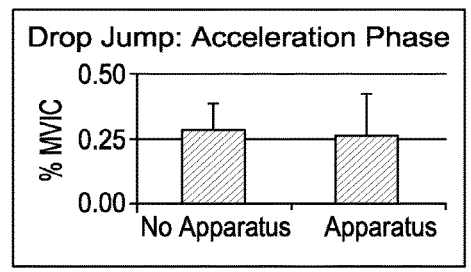
Figure 12A:
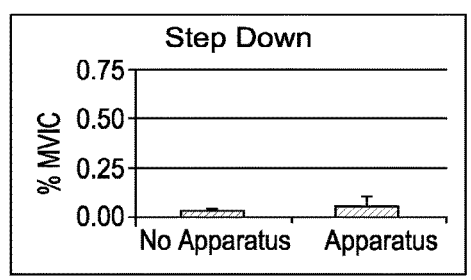
Figure 12B:
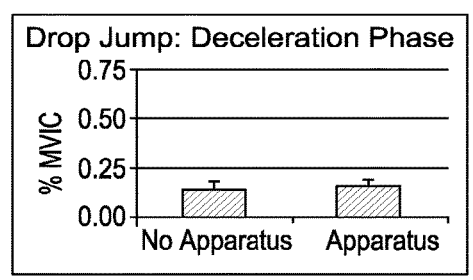
Figure 12D:
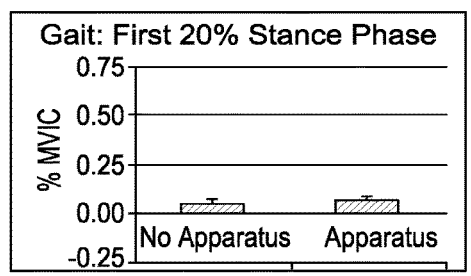
Figure 12C:
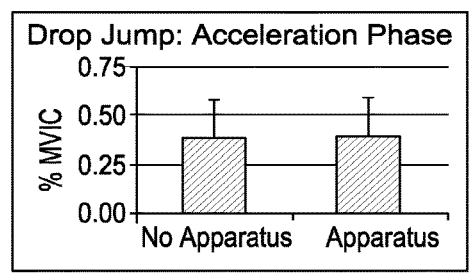

Referring to FIGS. 7*a-c*, in one embodiment, an actuator 80 is completely flat and is about 0.254 cm thick. It has the same perimeter dimensions as actuator 30 (FIGS. 6*a-f*) appears to have when viewed from directly above, i.e., actuator 80 has the same top profile as actuator 30, but is completely flat. However, because it is flattened, it has no curved top, concave or convex shape, or curved perimeter lip.

In another embodiment, an actuator (not shown) is completely flat and is about 0.254 cm thick, but has smaller length and width dimensions than actuator 80 (FIGS. 7*a-c*). Otherwise, it has the same relative shape dimensions as actuator 80. Such an actuator is about 8.59 cm long from end-to-end directly across its flattened surface, which is its longest dimension and runs along its lengthwise axis of symmetry. It has widths of approximately 6.20 cm and 4.78 cm at its respective widest and narrowest dimensions directly between two relatively straight tapering opposing sides. Its relatively straight opposing sides are connected at their relatively farther (separated by about 6.20 cm) and closer (about 4.78 cm) ends by respective rounded opposing side arcs, each of which, if extended, would define a circle respectively having a radius of about 3.8 cm or about 3.3 cm. Because the actuator is flat, it has no curved top or curved perimeter lip.

In one embodiment, actuator 30, 80 is made from up to about 0.254 cm injection molded 112 R-scale hardness (plus or minus at least about 5%) 6/6 ST 801 nylon, but may be made from anywhere between about 0.21 cm and about 0.64 cm at this hardness. As hardness varies, so may the relative thickness used, as long as it achieves some or all of the herein recited functions. Actuator 30 has a notched izod (ft/lb in.) of about 17.0 @ 73 deg F., a flex strength @ yield of about 9800 psi @ 73 deg F., and a tensile strength at yield of about 7500 psi @ 73 deg F. Other suitable materials and hardness, notched izod, flex strength, and/or tensile strength combinations are also appropriate.

An actuator may alternatively, for example, be made from injection molded 105 R-scale hardness (plus or minus at least about 5%) ABS 648. This embodiment has a notched izod (ft/lb in.) of about 6.75 @ 73 deg F., a flex strength @ yield of about 10000 psi @ 73 deg F., and a tensile strength at yield of about 5900 psi @ 73 deg F.

However, any rigid plastic material or similarly functioning material may be used, such as polyethylene, polyvinylchloride, or any other polymer or co-polymer resin. Also for example, treated natural wood, any foam injection resins (such as comprised, e.g., of the polymers stated above), hard rubber, composites, metals, or many other materials may be used. Any material suitable for performing any or all of the functions stated herein may be used, however.

In one embodiment, the actuator (not shown) is completely flat, although any low-profile shape may be used for this particular embodiment.

Hard plastic, and generally oval-shaped actuator 30 fits into the thigh sleeve component 20, in pocket 13.

In one embodiment, actuator 30 is positioned on other parts of the anterior side of a thigh.

Actuator 30 may or may not be inside a pocket in either sleeve 10, wrap 40, or shorts 50.

In one embodiment, actuator 30, 80 is more directly or directly fastened at it edges or one or more of its relatively flat top or bottom sides to sleeve 10, wrap 40 or band wrap 60, bands 61, or strap 20, for example, by adhesive or pieces of hook and loop fabric.

In one embodiment, apparatus 1 has a non-slip inside finish such as a micro-fleece coated fabric or a "rubberized" fabric such as coated pigskin or FABRIFOAM® applied so as to help maintain its longitudinal and circumferential positioning with respect to a thigh without migrating, especially when used by over-weight individuals.

In an alternate embodiment, apparatus 1 is appended by a piece of fabric placed over the knee, even though strap 20 and/or actuator 30 do not impinge upon or touch the knee itself. Such an embodiment would for example comprise a sleeve extended below the thigh and over, and even below, the knee In another embodiment, apparatus 1, or any other embodiment, is part of a larger mechanical brace that fits about the knee.

Apparatus 1 is used with actuator 30, although in another embodiment, positive results are obtained using, for example, sleeve 10 and/or elastic strap 20 only.

EXAMPLES

The idea of treating such a wide variety of knee pain with a single device, as stated by one orthopedic surgeon who wore the device for his knee pain, "defies all his medical training[.]" The ability to relieve pain as dramatically and instantly as this embodiment of the present invention, combining high compression to the thigh, was not previously predicted. The use of strap 20 and/or actuator 30 positioned over the quadriceps at the muscular juncture described above, in combination with such compression was also not previously predicted.

Using a thigh sleeve alone is only useful for hamstring and quadriceps muscular injuries. The use of a device on a thigh to reduce articular joint pain, degenerative joint pain, and other types of knee pain—all of which are all non-muscular joint pain—is until now non-existent. The surprising nature of this discovery is all-the-more heightened when considering the additional use of strap 20 and/or actuator 30.

First, the entire idea of applying something to the thigh to relieve pain in the knee is original thinking. The combination of sleeve 10 with actuator 30 on a thigh is new. The location at which actuator 30 is placed is also new. Placing a convex actuator is counter-intuitive, but most effective. This component configuration of apparatus 1 will force the scientific and medical community to undertake an entire re-estimation in the use of traditional bracing for knee pain.

Not only is apparatus 1 and its combination of components new, it differs from conventional wisdom. From experts in the field of orthopedics, bracing, and research, descriptions of apparatus 1 have included, "it is amazing," "this defies conventional wisdom and science taught in medical school," and "this is snake oil and it works[.]" Conventional wisdom and thought has kept the industry away from placing knee pain treatment on the thigh largely because all of the thought and focus has been on the knee.

As seen in the comparative data below, the use of actuator 30, again, is counter-intuitive. There has not been any product or method that would lead one to apply a strap 20 around a thigh or place an actuator 30 over any portion of the quadriceps. Apparatus 1 has made the experts scratch their heads wondering how it works.

Preliminary testing nevertheless shows that apparatus 1 changes the firing pattern of the leg muscles, which includes a reduction of firing intensity of each major muscle except for the gluteus maximus, as shown in the following test results for healthy patients who do not experience knee pain.

Test subjects had no prior relationship with the inventor or his licensee, or in any other entity having a right to or an interest in this invention. Test subjects have no financial stake in the invention or any such entity, and have no known previous testing experience.

Firing Intensities of a Leg when Using Apparatus 1

Examples 1-5

Apparatus 1 was evaluated on patients who do not experience knee pain. Muscle activity associated with application of apparatus 1 was quantified using established electromyographic (EMG) techniques. Five subjects were instrumented for EMG testing. Bipolar surface electrodes were placed over the muscle belly of the following muscles on the subject's dominant leg: (1) vastus lateralis, (2) vastus medialis, (3) lateral hamstrings, (4) medial hamstrings, and (5) gluteus maximus. EMG signals were sampled at 1560 Hz while subjects performed the following activities: (1) walking at a self-selected speed, (2) step down from a 15.24 cm step, and (3) drop jump from a 35.56 cm box. In addition, subjects performed maximal voluntary isometric contractions for the knee flexors and extensors on a KINCOM™ Isokinetic Dynamometer, and the force produced for each muscle group was recorded. All subjects performed the above listed activities with and without the apparatus 1. The order of testing with and without apparatus 1 application was randomized for all subjects.

Referring to FIGS. 8*a-d*, 9*a-d*, 10*a-d*, 11*a-d*, and 12*a-d*, the following Tables 1-5 compare average EMG activity of leg muscles in the subjects, with and without apparatus 1:

TABLE 1

(FIGS. 8a-d: Vastus Lateralis)

| VL (% MVIC) | Step Down | Drop Jump: Decel. | Drop Jump: Accel. | Gait: $1^{st}$ 20% Stance |
|---|---|---|---|---|
| No App. | 23.4 ± 7.5 | 54.0 ± 21.3 | 82.4 ± 28.8 | 14.1 ± 10.9 |
| Apparatus | 19.2 ± 5.5 | 43.2 ± 17.6 | 72.4 ± 25.5 | 8.2 ± 5.1 |
| % Change | −17.9% | −20.0% | −12.1% | −22.7% |

TABLE 2

(FIGS. 9a-d: Vastus Lateralis)

| VM (% MVIC) | Step Down | Drop Jump: Decel. | Drop Jump: Accel. | Gait: 1$^{st}$ 20% Stance |
|---|---|---|---|---|
| No App. | 27.2 ± 5.8 | 61.9 ± 24.7 | 86.7 ± 19.0 | 9.3 ± 5.0 |
| Apparatus | 19.6 ± 11.0 | 57.6 ± 26.4 | 81.1 ± 13.2 | 7.1 ± 6.6 |
| % Change | −27.9% | −6.9% | −6.5% | −23.6% |

TABLE 3

(FIGS. 10a-d: Lateral Hamstrings)

| LH (% MVIC) | Step Down | Drop Jump: Decel. | Drop Jump: Accel. | Gait: 1$^{st}$ 20% Stance |
|---|---|---|---|---|
| No App. | 6.9 ± 2.0 | 12.8 ± 5.0 | 28.5 ± 4.9 | 9.5 ± 5.2 |
| Apparatus | 5.0 ± 2.0 | 11.3 ± 4.6 | 24.5 ± 1.6 | 8.5 ± 3.6 |
| % Change | −27.5% | −11.7% | −14% | −10.5% |

TABLE 4

(FIGS. 11-a-d: Medial Hamstrings)

| MH (% MVIC) | Step Down | Drop Jump: Decel. | Drop Jump: Accel. | Gait: 1$^{st}$ 20% Stance |
|---|---|---|---|---|
| No App. | 12.2 ± 5.2 | 13.8 ± 5.7 | 27.6 ± 10.5 | 12.8 ± 4.8 |
| Apparatus | 9.1 ± 3.9 | 11.8 ± 3.6 | 25.6 ± 16.1 | 13.9 ± 3.7 |
| % Change | −25.4% | −14.5% | −7.2% | +8.5% |

TABLE 5

(FIGS. 12a-d: Gluteus Maximus)

| GMAX (% MVIC) | Step Down | Drop Jump: Decel. | Drop Jump: Accel. | Gait: 1$^{st}$ 20% Stance |
|---|---|---|---|---|
| No App. | 3.5 ± 0.7 | 13.9 ± 4.1 | 38.1 ± 19.4 | 5.6 ± 1.6 |
| Apparatus | 5.1 ± 4.7 | 15.7 ± 2.8 | 38.7 ± 19.2 | 6.6 ± 2.6 |
| % Change | 45.7% | 12.9% | 1.6% | 17.9% |

Figure 13A:
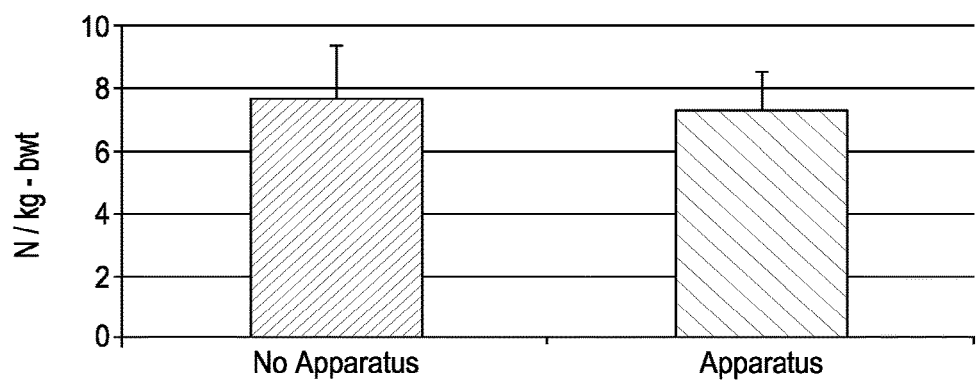

Referring to FIGS. 13a and b, the following Table 6 compares average quadriceps and hamstrings muscle force normalized to body weight, with and without apparatus 1:

TABLE 6

Figure 13B:
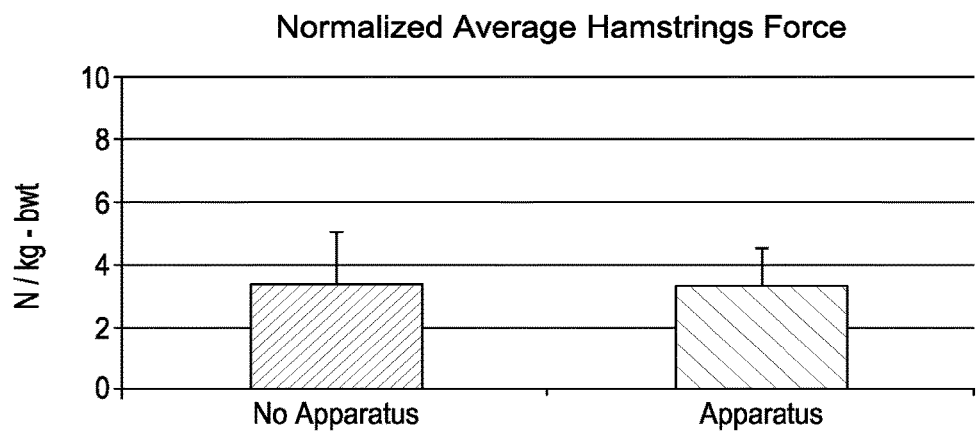

(FIGS. 13 a-b)

|  | Quadriceps Force (N/kg) | Hamstrings (N/kg) |
|---|---|---|
| No App. | 7.75 ± 1.6 | 3.34 ± 1.2 |
| Apparatus | 7.33 ± 1.2 | 3.26 ± 0.9 |

Overall, subjects demonstrated a decrease in muscle activity for all the thigh muscles (the vastus lateralis, vastus medialis, lateral hamstrings, and medial hamstrings), but an increase for the gluteus maximus muscle while wearing apparatus 1. When averaged across all activities, vastus lateralis and vastus medialis activity decreased 18.2% and 16.2%, respectively. On average, the lateral and medial hamstring muscle activity decreased 15.9% and 9.6%, respectively. Only the gluteus maximus demonstrated an increase in activation following application of the compression sleeve (19.5% increase across all activities). Thus, the apparatus improved gluteus maximus force by at least about 45% during step down (about 17.9% for gait at first 20% of stance), which muscle is believed to be primarily responsible for a general stabilization of the knee.

While there was an overall decrease in thigh muscle activity while subjects were wearing apparatus 1, there was only a slight decrease in force production at the knee. On average there was a 5.4% decrease in force production of the knee extensors (during knee extension) and a 2.4% decrease in force production of the knee flexors (during knee flexion) while subjects were wearing apparatus 1. In conclusion, application of apparatus 1 led to an overall decrease in muscle activity; however in these examples this change in muscle activation did not appear to result in a meaningful change in muscle force production during knee flexion/extension.

It appears from the above that apparatus 1 causes reduced firing activity on the vastus medialis obliquus and increased overall firing activity on a lateral mechanism in the knee, such as on the vastus lateralis and the gluteus maximus. It is believed that reducing the load in the rectus femoris and/or the vastus medialis obliquus, and increasing the lateral mechanism, may preserve previously over-utilized or damaged tissue in favor of less-utilized and less-damaged tissue, thereby causing the results shown herein.

Thus, one aspect of the invention is directed to reducing the firing of the vastus medialis obliquus and increasing the firing activity of muscles in the lateral mechanism of the knee, such as the vastus lateralis and gluteus maximus.

Pain Reduction

Examples 6-42

It is believed that there are several muscular and neural effects occurring on a knee while wearing apparatus 1. Apparatus 1 is believed to provide an improvement in muscular function that leads to the sensation of more stability. Several wearers who had been wearing a rigid brace felt an immediate relative improvement in perceived knee stability. The most profound effect, however, was in the reduction of knee pain.

Thirty-seven participants were tested for reduced knee pain when using apparatus 1. There were three categories of test subjects, (1) osteo-arthritis (Examples 6-13), (2) patelolofemoral pain (Examples 14-28), and (3) general knee pain (Examples 29-42). As seen below, the average percentages of pain reduction were at least about 83%, at least about 79%, and at least about 75%, respectively. The test was a standard stair step test used in diagnosing knee pain and symptoms. Each patient stepped down from a 17.78 cm stair using the affected knee's leg, touched the heel of the opposing non-affected knee's leg to the ground, and then raised it back to the starting position on the stair, and repeated if pain was tolerable. This isolated joint pain and used an analog scale from 0-10, with "10" representing unbearable pain, "1" representing slight-to-no pain, and "0" representing no pain at all (a 100% reduction in pain). The test was always first performed without wearing apparatus 1 on a first set of stair steps followed by wearing apparatus 1 on a next set. Each time with and without the device, the patient was asked to rate the pain on a 0-10 scale. When apparatus 1 was applied to the leg before the step test, the wearer was asked to walk around for a minute to get accustomed to the feeling of the apparatus 1, at which point many individuals commented that the device made their leg feel "springy."

Up to this point, preliminary testing has shown apparatus 1 to be effective at least in reducing pain in patellofemoral dysfunction, PF osteoarthritis, femorotibial osteoarthritis, general knee pain, post total knee, post-op knee with ongoing pain, and post-traumatic knee pain. These preliminary test results show apparatus 1 to have about a 74% reduction in varied chronic and acute knee pain. Nearly each person (to date, approximately 40 people have been tested) who has worn apparatus 1 has experienced almost immediate relief, that is, from about 50% relief to total relief. In particular, to date, people suffering from the most severe cases of pain, who have worn apparatus 1 have stopped using heavy prescription pain medications. (One person took daily pain medications for nine years and another for ten years, which have now been eliminated). Half of the other subjects use periodic over-the-counter pain medications, such as acetaminophen (e.g., TYLENOL® pain reliver). These users have experienced dramatic reductions in their need for such medications.

The following are data comparing pain first without, then with, the apparatus 1, wherein pain was rated by subjects on a 0-10 pain scale after five repetitions (or less, if not tolerable) of knee flexion, step down, opposing heel strike, and effected knee extension to raise the opposing heel to the starting position. Subject knees were generally categorized (as seen below) as having undergone previous surgery ("1"), osteoarthritis (a/k/a OA and "2" below), patella-femoral pain and patellofemoral osteoarthritis (a/k/a/ PFOA and "3"), total knee arthroplasty (a/k/a TKA and "4"), and general knee pain (a/k/a "5" below):

| EX. | General Description of Pain | General Category | Weight | Age & Sex (m/f) | Pain Rating w/o Device | Pain Rating with Device | % Pain Reduction |
|---|---|---|---|---|---|---|---|
|  | OA PAIN |  |  |  |  |  |  |
| 6 | OA, TKA candidate, severe varus | 2 | 185 | 71 m | 7 | 1 | 86% |
| 7 | Degenerative knee, PFOA, more pain lately, two steroid injections, 800 mg ibuprof. daily | 2 | 235 | 57 m | 4 | 2 | 50% |
| 8 | Chronic Pain, likely OA, methadone 2x daily | 2 | 200 | 52 m | 7 | 0 | 100% |
| 9 | OA, TKA candidate | 2 | 125 | 78 f | 5 | 1 | 80% |
| 10 | TKA scheduled, OA | 2 | 240 | 61 f | 6 | 1 | 83% |
| 11 | PF, OA | 3 | 172 | 73 m | 5 | 0 | 100% |
| 12 | OA, wears OA unloader | 2 | N/A | 41 f | 3 | 2 | 42% |
| 13 | OA | N/A | N/A | 61 f | 6 | 2 | 66% |
|  | Total |  |  |  | 34 | 5 | 83% |
|  | PF PAIN |  |  |  |  |  |  |
| 14 | Chronic PF pain | 3 | 160 | 54 f | 3 | 0 | 100% |
| 15 | Chronic PF pain since high-school | 3 | 170 | 40 f | 4 | 2 | 50% |
| 16 | Recurrent patella dislocation & associated pain | 3 | 120 | 40 f | 4 | 0 | 100% |
| 17 | Chronic PF pain, Skill Saw ® accident five years previous | 3 | 180 | 43 m | 5 | 1 | 80% |
| 18 | Chronic PF pain w/lateral offset & tilt | 3 | 340 | 53 f | 7 | 1 | 86% |
| 19 | Chronic PF pain w/lateral offset & tilt | 3 | 330 | 51 f | 5 | 2 | 60% |
| 20 | Patella dislocation | 3 | 115 | 15 f | 6 | 1 | 83% |
| 21 | Scheduled for lateral realign. surgery, chronic PF pain, worn post-op for pain reduction and mobility | 3 | 125 | 16 f | 8 | 2 | 75% |
| 22 | PF pain | 3 | 200 | 64 f | 6 | 2 | 67% |
| 23 | PF pain | 3 | 95 | 52 f | 3 | 0 | 100% |
| 24 | Degenerative knee, PF pain, forced reduction in activity | 3 | 200 | 52 m | 6 | 1 | 83% |
| 25 | PF pain, post ACL procedure | 3 | 210 | 55 m | 5 | 1 | 80% |
| 26 | Chronic PF Pain | 3 | 230 | 41 m | 6 | 2 | 67% |
| 27 | PF pain | 3 | 140 | 68 f | 5 | 0 | 100% |
| 28 | PF | 3 | 170 | 45 m | 4 | 2 | 50% |
|  | Total |  |  |  | 77 | 17 | 79% |
|  | General Knee Pain |  |  |  |  |  |  |
| 29 | Nine year post injury. 3 surgeries. Meniscus allograft. Currently wears OA unloader brace, Darvocet ® 1x daily | 1,5 | 150 | 42 f | 8 | 1 | 88% |
| 30 | lateral realign., osteotomy, patella relocat, 2 surgeries | 1,5 | 135 | 18 f | 4 | 1 | 75% |
| 31 | Seven surgeries, 2-TKA with one revision | 1,5 | 190 | 59 f | 4 | 1 | 75% |

-continued

| EX. | General Description of Pain | General Category | Weight | Age & Sex (m/f) | Pain Rating w/o Device | Pain Rating with Device | % Pain Reduction |
|---|---|---|---|---|---|---|---|
| 32 | ACL deficient, torn meniscus, 30-yr-old injury | 5 | 245 | 54 m | 7 | 2 | 71% |
| 33 | Stiffness, swelling, clicking, likely loose body in knee | 5 | 130 | 44 f | 4 | 1 | 75% |
| 34 | Medial joint pain with swelling for 6 years | 5 | 145 | 40 f | 2 | 1 | 50% |
| 35 | General knee pain, 2 menisectomies | 1,5 | 200 | 58 m | 5 | 2 | 60% |
| 36 | Retro-patella pain possible patella fat pad, swelling | 5 | 125 | 16 f | 9 | 8 | 11% |
| 37 | Patella tendon rupture | 1,5 | 235 | 38 m | 8 | 5 | 38% |
| 38 | Traumatic ACL/PCL/LCL/MCL rupture | 1,5 | 195 | 30 m | 7 | 4 | 43% |
| 39 | ACL/LCL instability | 5 | 170 | 45 m | 5 | 0 | 100% |
| 40 | ACL replacement on same knee twice | 1,5 | 195 | 47 m | 7 | 3 | 57% |
| 41 | Rafting injury MCL/meniscus problem with constant pain | 5 | 185 | 53 f | 5 | 2 | 60% |
| 42 | Fractures tibia/fibia/patella, four years post op | 5 | 165 | 30 m | 5 | 0 | 100% |
| | Total | | | | 80 | 31 | 75% |

Thus, particular pain relief (in percentage reduction) has been shown to be between from at least about 11 to about 38, about 11 to about 43, ("about" for all the range end points in this paragraph, etc.) 11-50, 11-57, 11-60, 11-67, 11-71, 11-75, 11-80, 11-83, 11-86, 11-88, 11-100, 38-43, 38-50, 38-57, 38-60, 38-67, 38-71, 38-75, 38-80, 38-83, 38-86, 38-88, 38-100, 43-50, 43-57, 43-60, 43-67, 43-71, 43-75, 43-80, 43-83, 43-86, 43-88, 43-100, 50-57, 50-60, 50-67, 50-71, 50-75, 50-80, 50-83, 50-86, 50-88, 50-100, 57-60, 57-67, 57-71, 57-75, 57-80, 57-83, 57-86, 57-88, 57-100, 60-67, 60-71, 60-75, 60-80, 60-83, 60-86, 60-88, 60-100, 67-71, 67-75, 67-80, 67-83, 67-88, 67-100, 71-75, 71-80, 71-83, 71-86, 71-88, 71-100, 75-80, 75-83, 75-88, 75-100, 80-83, 80-86, 80-88, 80-100, 83-86, 83-88, 83-100, 86-88, 86-100, and 88-100.

A reduction in pain by a percentage or range of percentages indicated by any and/or all of the following ranges shall be deemed to be a therapeutically effective amount of pain reduction as used herein—exactly or about (for all the range end points in this paragraph):
11-38, 11-43, 11-50, 11-57, 11-60, 11-67, 11-71, 11-75, 11-80, 11-83, 11-86, 11-88, 11-100, 38-43, 38-50, 38-57, 38-60, 38-67, 38-71, 38-75, 38-80, 38-83, 38-86, 38-88, 38-100, 43-50, 43-57, 43-60, 43-67, 43-71, 43-75, 43-80, 43-83, 43-86, 43-88, 43-100, 50-57, 50-60, 50-67, 50-71, 50-75, 50-80, 50-83, 50-86, 50-88, 50-100, 57-60, 57-67, 57-71, 57-75, 57-80, 57-83, 57-86, 57-88, 57-100, 60-67, 60-71, 60-75, 60-80, 60-83, 60-86, 60-88, 60-100, 67-71, 67-75, 67-80, 67-83, 67-88, 67-100, 71-75, 71-80, 71-83, 71-86, 71-88, 71-100, 75-80, 75-83, 75-88, 75-100, 80-83, 80-86, 80-88, 80-100, 83-86, 83-88, 83-100, 86-88, 86-100, and 88-100.

Performance Increases

Examples 43-48

Initial testing has further shown, quite unexpectedly, with healthy conditioned athletes that apparatus 1 increases the tested athletes' standing long jump performance by an average of 3.5%.

A performance summary of three healthy athletes (two males and one female) when wearing and not wearing apparatus 1 was conducted. The first male athlete (Examples 43-44) was a high jumper. The second male athlete (Examples 45-46) was a football player. The female athlete (Examples 47-48) was a basketball player.

Each athlete performed eight total jumps, divided into two sets of four jumps per set. The first set consisted of one jump without apparatus 1, followed by two jumps with it, followed by one jump without it. The second set consisted of one jump with apparatus 1, followed by one jump without it, followed by one jump with apparatus 1, followed by one jump without it. Each athlete warmed up before the first jump with stretching, minimal jogging, and jumping. Conditioning for the athletes is at a high degree so fatigue is not an issue. Measurements were made in inches, but converted to centimeters.

Performance summary of apparatus 1 for standing broad jump

| Ex. | Set No. | Without App. | With App. | With App. | Without App. | Total Change (cm) | % Chg. | % Chg. | Average Chg. |
|---|---|---|---|---|---|---|---|---|---|
| 43 | 1 | 284.48 | 292.1 | 297.18 | 284.48 | 20.32 | 2.7% | 4.5% | 2.4% |
| 44 | 2 | 287.02 | 294.64 | 292.1 | 292.10 | 7.62 | 2.7% | 0.0% | |
| 45 | 1 | 273.05 | 287.02 | 306.07 | 284.48 | 35.56 | 5.1% | 7.6% | 4.2% |
| 46 | 2 | 302.26 | 304.8 | 312.42 | 302.26 | 12.70 | 0.8% | 3.4% | |

-continued

Performance summary of apparatus 1 for standing broad jump

| Ex. | Set No. | Without App. | With App. | With App. | Without App. | Total Change (cm) | % Chg. | % Chg. | Average Chg. |
|---|---|---|---|---|---|---|---|---|---|
| 47 | 1 | 210.82 | 213.36 | 228.6 | 209.55 | 21.59 | 1.2% | 9.1% | 3.9% |
| 48 | 2 | 220.98 | 220.98 | 223.52 | 212.09 | 11.43 | 0.0% | 5.4% | |
| Total | | 1578.61 | 1612.90 | 1659.89 | 1584.96 | 109.22 | 2.2% 2.1% | 4.7% 5.0% | 3.5% |

Overall improvement by using apparatus 1 was at least about 3.5%. Set 1 improvement was by at least about 2.2% and set 2 improvement was by at least about 5.0%. All athletes improved. The least improvement was by at least about 2.4%, followed by at least about 3.9%; then the highest improvement was by at least about 4.2%. Thus, improvement from these examples was from, on average, about 2.4% to about 4.2%. Total improvement with 24 jumps by all athletes was 109.22 cm.

Thus, particular increases in actual optimal performance levels (in percentages) has been shown to be between from at least about 0 to about 0.8, about 0to about 1.2, about 0to about 2.7, about 0to about 3.4, (about for all of range end points in this paragraph . . . ) 0-4.5, 0-5.1, 0-5.4, 0-7.6, 0-9.1, 0.8-1.2, 0.8-2.7, 0.8-3.4, 0.8-4.5, 0.8-5.1, 0.8-5.4, 0.8-7.6, 0.8-9.1, 1.2-2.7, 1.2-3.4, 1.2-4.5, 1.2-5.1, 1.2-5.4, 1.2-7.6, 1.2-9.1, 2.7-3.4, 2.7-4.3, 2.7-5.1, 2.7-5.4, 2.7-7.6, 2.7-9.1, 3.4-4.5, 3.4-5.1, 3.4-5.4, 3.4-7.6, 3.4-9.1, 4.5-5.1, 4.5-5.4, 4.5-7.6, 4.5-9.1, 5.1-5.4, 5.1-7.6, 5.1-9.1, 5.1-7.6, 5.1-9.1, 5.4-7.6, 5.4-9.1, and 7.6-9.1.

Devices placed on the legs are usually viewed as being heavy, bulky, or awkward and not desirable for use during competition. Apparatus 1 is so unobtrusive that all the tested athletes have felt nothing but the positive effects on performance derived from wearing apparatus 1.

When worn, a leg with apparatus 1 very often immediately feels more "springy." During the swing phase in a wearer's stride while walking, a leg appears to be spring-loaded so as to make a knee on the same leg swing forward with less effort. It has been observed that corresponding knees actually lift higher off the ground, thereby raising the foot higher.

This enhanced feeling of being "springy" was most pronounced when applied to an individual who was in a motor scooter accident four years ago and was left with fractures in the patella, tibia, and fibular. Along with this the wearer had neurological deficit in the affected leg which caused an inability to properly lift the leg while walking. Immediately after applying the device the wearer's gait changed and was able to lift the foot adequately off the floor so as not to drag the toes and heel.

A second aspect of the present invention is directed to a method of reducing knee pain and/or increasing athletic performance that includes any combination of the embodiments, features, components, and techniques, substantially as described above. Other embodiments, techniques, or devices can also be used together or alternately in this method aspect of the invention.

While it is apparent that illustrative embodiments are disclosed herein, it is appreciated that numerous modifications and other embodiments may be devised by those skilled in the art. Additionally, feature(s), and/or element(s) from any embodiment may be used singly or in combination with other embodiment(s). Therefore, it will be understood that the appended claims are intended to cover all such modifications and embodiments that would come within their scopes.

I claim:

1. An apparatus for reducing knee pain, comprising:
    a compressive element configured to fit over and around a mid portion of a thigh of a leg and to be positioned above a knee joint of the leg; and
    an elastic strap configured to fit tightly and circumferentially over and around the compressive element, above the knee joint at the mid portion of the thigh at a location that extends over an intersection of a rectus femoris muscle, a sartorius muscle and a vastus medialus obliquus muscle of the thigh; and
    a hard actuator configured to:
        be positioned beneath the elastic strap, at a location adjacent to the intersection of the rectus femoris muscle, the sartorius muscle and the vastus medialus obliquus muscle; and
        press against the intersection of the rectus femoris muscle, the sartorius muscle and the vastus medialus obliquus muscle or to a location adjacent to the intersection to reduce or eliminate pain in the knee joint.

2. The apparatus of claim 1, wherein the elastic strap is configured to extend entirely around the thigh.

3. The apparatus of claim 2, wherein the elastic strap is configured to wrap multiple times around the thigh.

4. The apparatus of claim 1, wherein the hard actuator includes a concave side configured to face the compressive element, over the intersection of the rectus femoris muscle, the sartorius muscle and the vastus medialus obliquus muscle.

5. A method of reducing knee pain or increasing athletic performance that uses an apparatus according to claim 1.

6. An apparatus according to claim 1, wherein the compressive element, the elastic strap and the hard actuator are configured to increase athletic performance when properly positioned over the mid portion of the thigh.

7. The apparatus of claim 1, comprising a plurality of elastic straps.

8. An apparatus for reducing knee pain, increasing athletic performance or stabilizing a knee, comprising:
    a compressive element configured to fit over a thigh of at least one leg;
    an elastic strap configured to fit tightly and circumferentially over and around the compressive element at a location over a mid portion of the thigh and above a knee joint adjacent to the thigh; and
    a hard actuator positioned beneath the elastic strap at a location that will place the hard actuator over an anterior side of the mid portion of the thigh upon proper placement of the compressive element on the thigh and that will press against the anterior side of the mid portion of the thigh upon wrapping the elastic strap around the mid portion of the thigh.

9. The apparatus of claim 8, wherein the hard actuator is located and configured to be positioned approximately over an intersection of a rectus femorus muscle of the thigh, a sartorius muscle of the thigh and a vastus medialus obliquus muscle of the thigh and the elastic strap is located and configured to press the hard actuator against the thigh to reduce or eliminate pain in the knee joint.

10. The apparatus of claim 8, wherein the mid portion of the thigh is a distal third of the thigh.

11. A method of reducing knee pain or increasing athletic performance that uses an apparatus according to claim 8.

12. An apparatus for reducing knee pain, comprising:
a thigh component configured to fit over a thigh of at least one leg;
an elastic strap configured to fit circumferentially over the thigh component, around a mid portion of a single thigh and above a knee joint adjacent to the thigh; and
an actuator with a side configured to face the thigh and to press against and to apply localized pressure against an anterior side of a mid portion of the thigh by the strap at a location that will reduce or eliminate pain in the knee joint.

13. The apparatus of claim 12, wherein the actuator includes at least one enclosed volume.

14. The apparatus of claim 12, wherein the side of the actuator is convex or flat.

15. A method of reducing knee pain or increasing athletic performance that uses an apparatus according to claim 12.

16. An apparatus for reducing knee pain, comprising:
a compressive element configured to fit over a thigh of at least one leg without extending over opposed lateral and medial sides of a knee joint adjacent to the thigh;
an elastic strap configured to wrap circumferentially around the compressive element on a single thigh, above a knee joint only at a mid portion of the thigh; and
a hard actuator positioned and oriented to face an anterior side of the mid portion of the thigh and to be pressed by the elastic strap toward the anterior side of the mid portion of the thigh to apply a localized pressure to the anterior side of the mid portion of the thigh and to reduce or eliminate pain in the knee joint.

17. A method of reducing knee pain or increasing athletic performance that uses an apparatus according to claim 16.

18. The apparatus of claim 16, wherein the apparatus is configured to be positioned without extending over a medial side of the knee joint or lateral side of the knee joint and without directly anatomically aligning a patella, a femoral condyle or a tibial condyle with another portion of the knee joint.

* * * * *